US011921041B2

(12) United States Patent
Ledru et al.

(10) Patent No.: US 11,921,041 B2
(45) Date of Patent: Mar. 5, 2024

(54) METHOD AND SYSTEM FOR VISUALIZATION OF ENDOTOXINS IN A FLUID SAMPLE

(71) Applicant: BL TECHNOLOGIES, iNC., Minnetonka, MN (US)

(72) Inventors: Sukmi Ledru, Boulder, CO (US); Krzysztof Franaszczuk, Boulder, CO (US); Jesse Manley, Boulder, CO (US); David Kremer, Boulder, CO (US); Vamsi Panuganti, Boulder, CO (US); Jeremiah Teague, Boulder, CO (US); Yan Le, Boulder, CO (US); Michael Scaer, Boulder, CO (US)

(73) Assignee: BL Technologies, Inc., Minnetonka, MN (US)

( * ) Notice: Subject to any disclaimer, the term of this patent is extended or adjusted under 35 U.S.C. 154(b) by 253 days.

(21) Appl. No.: 17/437,117

(22) PCT Filed: Mar. 9, 2020

(86) PCT No.: PCT/US2020/021642
§ 371 (c)(1),
(2) Date: Sep. 8, 2021

(87) PCT Pub. No.: WO2020/185646
PCT Pub. Date: Sep. 17, 2020

(65) Prior Publication Data
US 2022/0178826 A1    Jun. 9, 2022

Related U.S. Application Data

(60) Provisional application No. 62/826,355, filed on Mar. 29, 2019, provisional application No. 62/815,716, filed on Mar. 8, 2019.

(51) Int. Cl.
*G01N 21/64* (2006.01)
*G01N 21/27* (2006.01)
(Continued)

(52) U.S. Cl.
CPC ....... *G01N 21/6452* (2013.01); *G01N 21/272* (2013.01); *G01N 21/77* (2013.01);
(Continued)

(58) Field of Classification Search
CPC .. G01N 21/6452; G01N 21/272; G01N 21/77; G01N 33/579; G01N 2201/122;
(Continued)

(56) References Cited

U.S. PATENT DOCUMENTS

2011/0201015 A1 *  8/2011  Yabusaki ......... G01N 33/54313
                                                    435/7.1
2012/0100624 A1    4/2012  Hara et al.
(Continued)

FOREIGN PATENT DOCUMENTS

CN    103339631 A    10/2013
EP    3935393 A1 *   1/2022   ........... G01N 21/272
(Continued)

OTHER PUBLICATIONS

Extended European Search Report, dated Nov. 4, 2022, received in connection with corresponding EP Patent Application No. 20770193.9.
(Continued)

*Primary Examiner* — David P Porta
*Assistant Examiner* — Gisselle M Gutierrez
(74) *Attorney, Agent, or Firm* — Meunier Carlin & Curfman LLC

(57) ABSTRACT

Exemplified methods and systems facilitate presentation of data derived from measurements of endotoxins in fluid samples. In particular, the exemplified methods and systems
(Continued)

facilitate presentation of such measurements in a graphical user interface and/or in a report for endotoxin concentrations in a fluid sample. The presentation facilitates a unified and intuitive graphic visualization that are presented within a single interactive interface and/or report.

25 Claims, 30 Drawing Sheets

(51) Int. Cl.
*G01N 21/77* (2006.01)
*G01N 33/579* (2006.01)
*G16H 10/40* (2018.01)
*G16H 15/00* (2018.01)
*G16H 20/17* (2018.01)
*G16H 40/63* (2018.01)

(52) U.S. Cl.
CPC .......... *G01N 33/579* (2013.01); *G16H 10/40* (2018.01); *G16H 15/00* (2018.01); *G16H 20/17* (2018.01); *G16H 40/63* (2018.01); *G01N 2201/122* (2013.01)

(58) Field of Classification Search
CPC .. G01N 21/253; G01N 2400/50; G16H 10/40; G16H 15/00; G16H 20/17; G16H 40/63
See application file for complete search history.

(56) References Cited

U.S. PATENT DOCUMENTS

| | | |
|---|---|---|
| 2013/0018618 A1 | 1/2013 | Eshima et al. |
| 2013/0254703 A1 | 9/2013 | Arling et al. |
| 2015/0260719 A1* | 9/2015 | Godec .............. G01N 33/56911 436/63 |
| 2018/0217172 A1 | 8/2018 | Webster et al. |
| 2023/0001409 A1* | 1/2023 | Clay ................ G01N 35/00693 |

FOREIGN PATENT DOCUMENTS

| | | | |
|---|---|---|---|
| FR | 3125336 A1 * | 1/2023 | ........... G01N 21/272 |
| JP | 2006275895 A | 10/2006 | |
| JP | 2007501020 A | 1/2007 | |
| JP | 2014140487 A | 8/2014 | |
| JP | 2015099160 A | 5/2015 | |
| JP | 2015127646 A | 7/2015 | |
| JP | 2015179022 A | 10/2015 | |
| WO | 2004065000 A1 | 8/2004 | |
| WO | 2008/139544 A1 | 11/2008 | |
| WO | 2012158308 A2 | 11/2012 | |
| WO | 2014058758 A1 | 4/2014 | |

OTHER PUBLICATIONS

Duquenne, P., et al., "Measurement of Endotoxins in Bioaerosols at Workplace: A Critical Review of Literature and a Standardization Issue," Annals of Occupational Hygiene, vol. 57, No. 2, 2013, pp. 137-172.
International Search Report and Written Opinion dated Jun. 2, 2020, from International Application No. PCT/US2020/021642, 11 pages.
Office Action issued for Chinese Application No. 202080018922.9, dated Dec. 23, 2023.
Communication Pursuant to Article 94(3) EPC, dated Dec. 1, 2023.
Noticeof Reasons for Refusal issued for Japanese Application No. 2021 553142, dated Dec. 5, 2023.

* cited by examiner

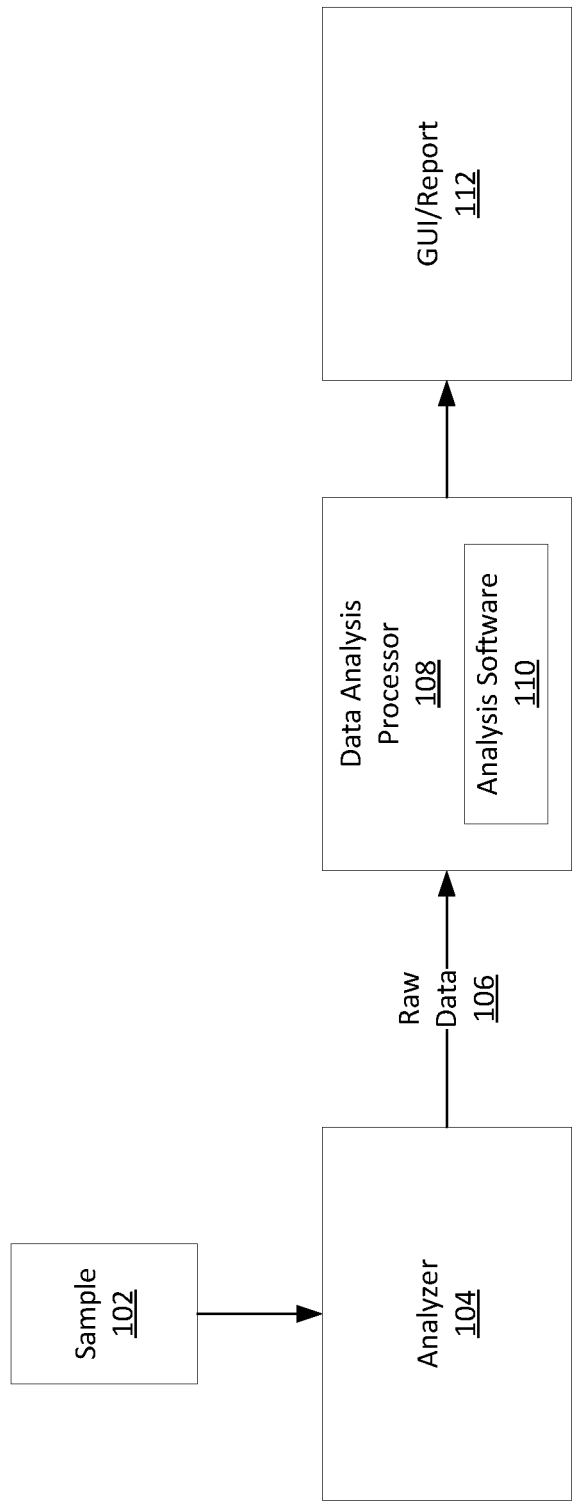

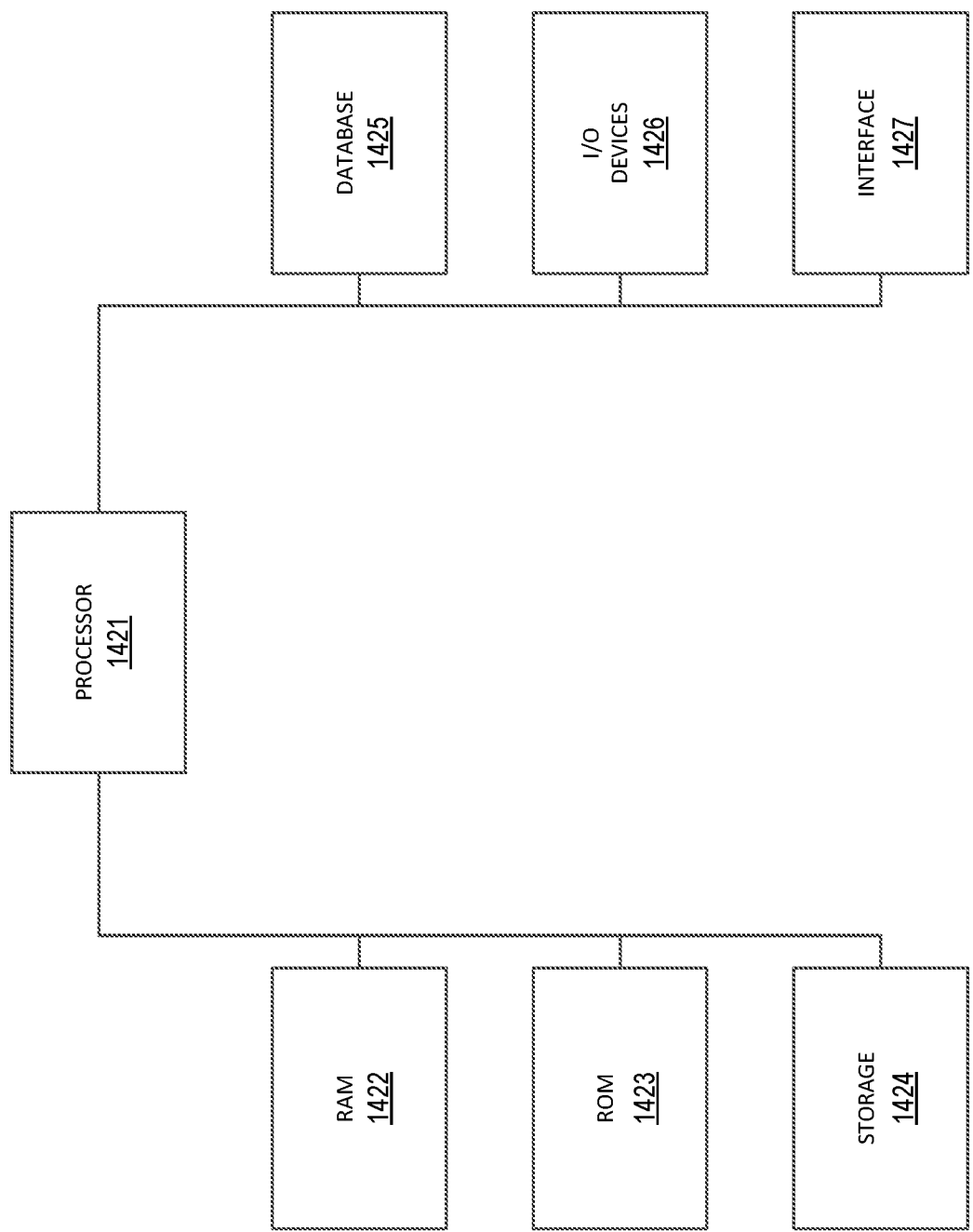

METHOD AND SYSTEM FOR VISUALIZATION OF ENDOTOXINS IN A FLUID SAMPLE

CROSS-REFERENCE TO RELATED APPLICATIONS

This National Stage application is a 371 of PCT application number PCT/US2020/021642, filed Mar. 9, 2020, entitled "Method and System for Visualization of Endotoxins in a Fluid Sample" which claims priority to, and the benefit of, U.S. Provisional Patent Application No. 62/815,716, filed Mar. 8, 2019, entitled "Method and System for Visualization of Endotoxins in a Fluid Sample"; and U.S. Provisional Patent Application No. 62/826,355, filed Mar. 29, 2019, entitled "Method and System for Visualization of Endotoxins in a Fluid Sample", each of which is incorporated by reference herein in its entirety.

BACKGROUND

Microbial contamination, such as Gram-positive bacteria, Gram-negative bacteria, yeast, and fungi may cause severe illness and even death in humans. When people become infected with gram negative bacteria, the bacteria may produce fever-inducing bacterial endotoxins. Endotoxins can be dangerous and even deadly to humans. Endotoxin molecules, which are lipopolysaccharide components of cell walls of gram negative bacteria, can be present in drug formulations and surfaces of medical devices, independent of microbial contamination. Endotoxin contamination can happen even if a system passes a sterility test, which is why an independent endotoxin test is required.

Currently, a variety of tests have been developed to detect the presence of endotoxin in or on the sample being tested using hemocyte lysates from horseshoe crabs. Clotting will occur when the hemocyte lysate is exposed to the endotoxin. Hemocyte lysate is amebocyte lysate produced from the hemolymph of various horseshoe crab species, including the *Limulus, Tachypleus*, and *Carcinoscorpius* species. A commonly used amebocyte lysate is produced from the hemolymph of Limulus, or Tachypleus species, is referred to as Limulus amebocyte lysate ("LAL"). Routine tests that use LAL include gel clot assays, end point turbidometric assays, kinetic turbidometric assays, endpoint chromogenic assays, and kinetical chromogenic assays. Tests that use LAL may also be used to test for certain types of glucans, markers for fungal contamination.

More information on LAL assays and the standards used may be found in United States Pharmacopeia ("USP") Chapter 85 "Bacterial Endotoxins Test" ("BET"), Japanese Pharmacopeia 4.01 "Bacterial Endotoxin Test", European Pharmacopoeia 2.6.14 "Bacterial Endotoxins", and other equivalent national Pharmacopeias. Additional internationally harmonized pharmacopeia information can be found in ICH Q4B Annex 14 "Bacterial Endotoxin Test General Chapter". For endotoxin testing in medical devices, information can be found in USP Chapter 161 "Transfusion and Infusion Assemblies and Similar Medical Devices" and ANSI/AAMI ST72 "Bacterial endotoxins—Test methods, routine monitoring, and alternatives to batch testing". These standards and procedures may be generally referred to as compendia.

Manufacturers in the pharmaceutical, medical device and food industries must meet certain standards to make sure their products do not contain microbial or endotoxin contamination. These industries require frequent, accurate, and sensitive testing for the existence of endotoxins to meet various safety standards, such as those set by the United States Food and Drug Administration, or the Environmental Protection Agency. These agencies accept many of the compendia procedures standards. Thus, if manufacturers want to obtain government approval to release a new product to market, many of the FDA requirements may be met if the products comply with the methods and standards in the compendia listed above. This can substantially reduce the cost to manufacturers to obtain FDA approval of new products.

These agencies also have strict reporting requirements when test results show bad results, or endotoxin concentrations outside the expected range. Such non-compliant results must be thoroughly investigated to find the root cause and explained to the regulating agency. This is time consuming and costly. If manufacturers can show the non-compliant result occurs because of an anomaly in the test itself, and not because of the presence of an endotoxin actually in or on the sample, many of the reporting requirements to the agencies may be satisfied. This may reduce the time and cost incurred to fulfill such reporting obligations. To date, there are no known methods or apparatuses that are capable of distinguishing between anomalies or errors in the test itself and an anomaly in the sample.

These assays in the various compendia require aqueous solutions comprising known concentrations of an endotoxin for use as standards. These aqueous solutions are typically unstable; therefore, they are usually made from powdered toxins at the test location just prior to testing. The LAL reagent also usually comes in powder form and must be reconstituted in an aqueous solution before use.

Preparation of the endotoxin and LAL powders is difficult due to the slow solvation of the critical biological molecules and their propensity to stick to surfaces during mixing and condense on surfaces afterwards. The LAL reagent also starts reacting slowly upon reconstitution and has a very short shelf life. While the best practice would be to mix these immediately before use, workflow typically dictates mixing them at the start of the process. Also, the process of preparation is prone to contamination from endotoxins which are ubiquitous in the environment.

The agencies also require a series of calibration tests to ensure the equipment and reagents used are functioning properly. The calibration tests and sample measurements must also be made more than once. The current laboratory method of complying with BET and other compendia is very detailed and requires repetitive and highly precise measuring of fluid volumes for distribution into multiple inlets of a microplate or the like without contamination.

The most common method of performing a LAL analysis is with a microwell plate and reader. A matrix of reaction wells, open at the top and with a clear window on the bottom, are placed in a heated spectrophotometric reader used for multiple, simultaneous assays. There are many drawbacks, including the lengthy time it takes to prepare the plate, its high cost, the opportunity for mistakes and contamination, and the need to have the work done by a technician specifically trained for and dedicated to this task.

Highly skilled operators are continuously monitored to ensure proper technique and accuracy of measurement and testing, and the operators are retrained as needed so as to ensure accuracy of the repetitive actions. Typical methods may have as many as 248 slow and time-consuming pipetting steps, making it an error prone method due to its complexity and contamination prone due to its length and number of manipulations.

Methods and devices have been developed to reduce the amount of steps or automated some or all of the steps in endotoxin testing. Some methods include automating one or more pipetting or aliquoting steps, automated mixing of samples, or preloading reagents in test substrates that allow only a very limited number of tests. All of the developed methods or devices, however, are missing one or more of the following aspects, low cost automation designed into the substrate, disposable clean substrate to insure cleanliness, compendial testing compliance on each substrate, built in individual test measurement validation, and simplicity of measurement operation.

Other microfluidic methods exist to partially automate the assay process, but these are not fully compatible with the compendia methods due to their limited size and their reliance on a stored calibration rather than on calibrations run at the same time in the same apparatus using the same reagents and standards. It also requires a precise sample measurement; no aliquots are generated by the instrument or apparatus itself.

Other automated methods rely on robotics to measure and distribute samples and reagents in a microplate. Once prepared, the plate is loaded in a reader, either manually or using another robot. The robot is typically a pipette-based dispensing system which accurately transfers samples and reagents from a vial rack to the plate, replacing pipette tips to prevent cross-contamination.

This is an expensive system which needs frequent validation of its robotic operations and multiple disposables (pipette tips, multiwall plates, dilution tubes, pipette filling trays, sampling vials, etc.) for each run. It also prepares the wells in sequence, and like manual preparation, cannot start all the reactions simultaneously. Contamination is still an issue and since the process is typically unmonitored, there is no legitimate way of rejecting contaminated samples for cause.

An automated system based on flow injection or sequential injection has also been developed. It uses disposable microfluidics which do not require cleaning and are not prone to contamination. This is a significant improvement in that it does analyses simultaneously and thus faster and as specified by compendia.

To date, however, there are no known methods or systems that facilitate presentation of data derived from the testing and analyzing the endotoxin concentration in a fluid sample.

There are also benefits to having improved visualization of testing progress of endotoxin testing.

SUMMARY

Exemplified methods and systems facilitate presentation of data derived from measurements of endotoxins in fluid samples. In particular, the exemplified methods and systems facilitate presentation of such measurements in a graphical user interface and/or in a report for endotoxin concentrations in a fluid sample. The presentation facilitates a unified and intuitive graphic visualization that are presented within a single interactive interface and/or report.

In some embodiments, a system is disclosed for testing of endotoxin in inject-able drug product or water. The system includes a processor and a memory having instructions stored thereon where execution of the instructions by the processor cause the processor to continuously obtain one or more data sets associated with measurement of a multi-well micro plate during acquisition of measurement of the multi-well micro plate, wherein each measurement is associated with a measured level (e.g., associated change in optical properties, e.g., absorbance, luminance, and/or fluorescence, etc.) of endotoxins reactions of i) endotoxins in an acquired sample of inject-able drug product or water to ii) one or more test reagents over time (e.g., wherein the injectable drug product or water comprises one or more reagents mixed with a drug or mixed with test the drug or water sample), where the data set includes a current measured level of endotoxin reactions for each well of the multi-well micro plate, wherein the multi-well micro plate comprises at least 96 wells. The instructions when executed by the processor cause the processor to singularly display, in a pane of a graphical user interface, from the obtained data set, a side-by-side graph comprising a plurality of visual elements, wherein each visual element of the plurality of visual elements is associated with the current measured level for the each well of the at least 96 wells of the multi-well micro plate, where each visual element of the plurality of visual elements comprises a vertically oriented bar that is configured to display data values spanning a range between a minimum value and a maximum value, where each of the minimum value and maximum value are aligned with a respective first and second horizontal line. The display further includes a visual element comprising a third horizontal line at a value that indicates an onset threshold of an endotoxin reaction for each, or among group of wells, of the at least 96 wells of the multi-well micro plate. The side-by-side graph of the at least 96 wells of the multi-well micro plate provides simultaneous comparison of a progress of endotoxin reaction in, or among group of wells of, the at least 96 wells of the multi-well micro plate to test endotoxin in the acquired sample of inject-able drug product or water.

In an aspect, a computer-implemented method is disclosed for formatting a display (e.g., a graphical user interface or a report) to present visualizations of endotoxin concentrations in a fluid sample, the method comprising generating, by a processor, for a graphical user interface or for a report, to be displayed on a stationary or mobile computing device, a graphical visualization, from a data set that identifies an optical density (OD) reading of a microplate comprising a plurality of optical wells, each optical well containing a fluid sample, said graphical visualization comprising a vertically-oriented bar graph having a plurality of vertical bars with at least one vertically-oriented bar graph for each optical well of the microplate, wherein the processor causes the vertically-oriented bar graph corresponding to the optical well of the microplate to increase vertically over time as a reaction between Limulus Amoebocyte Lysate (LAL) and bacterial endotoxin takes place in the optical well of the microplate, wherein a greater amount of endotoxin present in the optical well (whether related to samples, endotoxin standards, or positive product controls), the faster the reaction occurs with the LAL reagent, and subsequently the faster the processor causes the associated vertically-oriented bar graph to increase on the graphical visualization.

In some embodiments, the method further includes generating, by the processor, a horizontal line on the graphical visualization that represents a threshold OD or an onset OD, wherein a time at which vertically-oriented bar graph corresponding to an optical well reaches or passes the horizontal line is referred to as an "onset time" or a "reaction time" of the fluid sample in the optical well corresponding to the vertically-oriented bar graph that reached or passed the horizontal line.

In some embodiments, once the vertically-oriented bar graph reaches the horizontal line, the processor causes a color of the vertically-oriented bar graph to change from a first color to a second color.

In some embodiments, the first color is blue, and the second color is green.

In some embodiments, the method further includes generating, by the processor, vertically-oriented bar graphs representing endotoxin standards and negative controls that are also displayed on the graphical visualization.

In some embodiments, the vertically-oriented bar graphs representing endotoxin standards are labeled by the processor in a first color, vertically-oriented bar graphs representing negative controls are labeled by the processor in a second color, and the vertically-oriented bar graphs corresponding to the optical wells of the microplate are labeled by the processor in a third color.

In some embodiments, the vertically-oriented bar graphs representing endotoxin standards are labeled by the processor in a darker green, the vertically-oriented bar graphs representing negative controls are labeled by the processor in red, and the vertically-oriented bar graphs corresponding to the optical wells of the microplate are labeled by the processor in blue.

In some embodiments, the vertically-oriented bar graphs representing endotoxin standards are labeled by the processor in a darker green, the vertically-oriented bar graphs representing negative controls are labeled by the processor in red, and the vertically-oriented bar graphs corresponding to the optical wells of the microplate are labeled by the processor in lighter green.

In some embodiments, the vertically-oriented bar graphs representing endotoxin standards are labeled by the processor in a darker green, the vertically-oriented bar graphs representing negative controls are labeled by the processor in red, and the vertically-oriented bar graphs corresponding to the optical wells of the microplate are labeled by the processor in blue until they reach a horizontal line generated by the processor on the graphical visualization that represents a threshold OD or an onset OD, at which point the vertically-oriented bar graphs corresponding to the optical wells of the microplate are turned green by the processor.

In some embodiments, the method further includes generating, by the processor, the vertically-oriented bar graphs representing positive product controls on the graphical visualization.

In some embodiments, the vertically-oriented bar graphs representing positive product controls are labeled by the processor using a same color as used by the processor to label the vertically-oriented bar graphs corresponding to the optical wells of the microplate once the vertically-oriented bar graphs corresponding to the optical wells of the microplate reach a horizontal line generated by the processor on the graphical visualization, wherein the horizontal line represents a threshold OD or an onset OD.

In some embodiments, the vertically-oriented bar graphs representing positive product controls are labeled by the processor using a green color.

In some embodiments, positive product controls are calculated by the processor as: (endotoxin concentration in PPC−endotoxin concentration in sample)÷actual endotoxin concentration of a 0.5 EU/mL standard.

In another aspect, a system is disclosed that can perform any of the above method.

In another aspect, a non-transitory computer readable medium is disclosed comprising computer-executable instructions, wherein when executed, the computer-executable instructions cause the processor to perform any of the above method.

In another aspect, a report (e.g., a non-transitory report) is disclosed that is generated according to the above method.

In another aspect, a system is disclosed for testing of endotoxin in inject-able drug product or water, the system comprising a processor; and a memory having instructions stored thereon, wherein execution of the instructions by the processor, cause the processor to continuously obtain one or more data sets associated with measurement of a multi-well micro plate during acquisition of measurement of the multi-well micro plate, wherein each measurement is associated with a measured level (e.g., associated change in optical properties, e.g., absorbance, luminance, and/or fluorescence) of endotoxins reactions of i) endotoxins in an acquired sample of inject-able drug product or water to ii) one or more test reagents over time (e.g., wherein the injectable drug product or water comprises one or more reagents mixed with a drug or mixed with test the drug or water sample), and wherein the data set comprises a current measured level of endotoxin reactions for each well of the multi-well micro plate, wherein the multi-well micro plate comprises at least 96 wells; and singularly display, in a pane of a graphical user interface, from the obtained data set, a side-by-side graph comprising a plurality of visual elements, wherein each visual element of the plurality of visual elements is associated with the current measured level for the each well of the at least 96 wells of the multi-well micro plate, wherein each visual element of the plurality of visual elements comprises a vertically oriented bar that is configured to display data values spanning a range between a minimum value and a maximum value, wherein each of the minimum value and maximum value are aligned with a respective first and second horizontal line, wherein the display further comprises a visual element comprising a third horizontal line at a value that indicates an onset threshold of an endotoxin reaction for each, or among group of wells, of the at least 96 wells of the multi-well micro plate, and wherein the side-by-side graph of the at least 96 wells of the multi-well micro plate provides simultaneous comparison of a progress of endotoxin reaction in, or among group of wells of, the at least 96 wells of the multi-well micro plate to test endotoxin in the acquired sample of inject-able drug product or water.

In some embodiments, the side-by-side graph of the at least 96 wells of the multi-well micro plate provides indication of an improperly configured well, and wherein the indication is used to retest, or to evaluate retesting of, the sample of inject-able drug product or water in the improperly configured well in a subsequent test.

In some embodiments, the one or more data sets associated with measurement of the multi-well micro plate having the at least 96 wells are continuously obtained and displayed at a pre-defined interval of at least once a second (e.g., at every 5 seconds), wherein the interval is fixed to provide for observations of rate of endotoxin reactions in the at least 96 wells or a portion thereof.

In some embodiments, the instructions when executed by the processor cause the processor to receive input from an input device, wherein the input is associated with a cursor of the display; determine, in the pane of the graphical user interface, the cursor is placed on a visual element of the plurality of visual elements for at least one from the group consisting of selection of a visual element (e.g., via a mouse click or via a keyboard click) or for a pre-defined period of time (e.g., via a hovering action); and display, in the pane or in a second pane of the graphical user interface, i) a graph of the measured level of endotoxins reaction(s) over time for one or more wells that the cursor is placed or ii) measure parameter associated with the one or more wells that the cursor is placed.

In some embodiments, the graph of the measured level of endotoxin reaction(s) over time is presented, and wherein the graph comprises one or more kinetic curves over a period of reaction time for the selected well(s).

In some embodiments, the system further includes a display, the display having a horizontal pixel elements greater than twice a number of wells of the multi-well micro plate (e.g., to provide a bar having a pixel width greater than 2).

In some embodiments, the display has a set of vertical pixel elements, and wherein each of the plurality of visual elements spans at least 80% of the set of vertical pixel elements.

In some embodiments, a portion of the at least 96 wells of the multi-well micro plate includes a set of one or more standard wells, including a first standard well and a second standard well, wherein the visual elements associated with the first well and second well has a color that is different from the remainder of the at least 96 wells of the multi-well micro plate.

In some embodiments, the method further includes a sensor system configured to interrogate the at least 96 wells of the multi-well micro plate for measurement of the measured level of endotoxin reactions in the multi-well micro plate, wherein the sensor system comprises one or more sensors selected from the group consisting of an absorbance sensor, a fluorescence sensor, and a luminescence sensor.

In some embodiments, the sensor system is configured a 96-well micro plate.

In some embodiments, the sensor system is configured a 104-well micro plate.

In some embodiments, the measured level of endotoxin reactions comprises values associated with a measured change in transparency of the acquired sample of inject-able drug product or water associated with a reaction with the one or more test reagents.

In some embodiments, the measured level comprises values associated with a measured change in optical properties selected from the group consisting of, absorbance, luminance, fluorescent, and a combination thereof, of the acquired sample of inject-able drug product or water associated with a reaction with the one or more test reagents.

In some embodiments, the plurality of visual elements comprise a first set of visual elements associated with standard wells, a second set of visual elements associated with standard wells, a third set of visual elements associated with standard wells, a fourth set of visual elements associated with standard wells, a fifth set of visual elements associated with standard wells, and a sixth set of visual elements associated with standard wells, wherein the first set of visual elements has a 50-EU/ml standard, wherein the second set of visual elements has a 5-EU/ml standard, wherein the third set of visual elements has a 0.5-EU/ml standard, wherein the fourth set of visual elements has a 0.05-EU/ml standard, wherein the fifth set of visual elements has a 0.005-EU/ml standard, and wherein the sixth set of visual elements has a negative control standard.

In some embodiments, the value that indicates onset threshold is user-selectable.

In some embodiments, the instructions when executed by the processor cause the processor to receive input from an input device (e.g., mouse click on a GUI element, a short-cut key on the keyboard, etc.), wherein the input is associated with a selection of measurement parameter of the multi-well micro plate selected from the group consisting of: measured onset time, measured endotoxin concentration, measured positive product control (PPC) recovery, and determined matrix effect; obtain one or more second data sets associated with selected parameter; and display, in the pane or in a second pane of the graphical user interface, a second plurality of visual elements associated with the selected parameter, wherein the second plurality of visual elements have a number corresponding to the at least 96 wells, or a portion thereof, In another aspect, a method is disclosed to monitor testing of endotoxin in inject-able drug product or water, the method comprising obtaining, by a processor, one or more data sets associated with measurement of a multi-well micro plate, where each measurement is associated with a measured level of endotoxins in an acquired sample of inject-able drug product or water over time, wherein the data set comprises a current measured level for each well of the multi-well micro plate, wherein the multi-well micro plate comprises at least 96 wells; and singularly displaying, by the processor, in a pane of a graphical user interface, from the obtained data set, a side-by-side graph comprising a plurality of visual elements, wherein each visual element of the plurality of visual elements is associated with a current measured level of each of the at least 96 wells of the multi-well micro plate, wherein each visual element of the plurality of visual elements comprises a vertically oriented bar that is configured to span data values ranging between a minimum and a maximum value, wherein each of the minimum value and maximum value are coincident with a first and second horizontal line, wherein the display further comprises a visual element comprising a third horizontal line at a measured value that indicates onset threshold for each of the at least 96 wells of the multi-well micro plate, and wherein the side-by-side graph of the at least 96 wells of the multi-well micro plate provides simultaneous comparison of speed of reaction in, or among group of wells of, the at least 96 wells of the multi-well micro plate to monitor testing of endotoxin in the acquired sample of inject-able drug product or water.

In some embodiments, the method further includes interrogating the at least 96 wells of the multi-well micro plate for acquisition of the measured level of endotoxin reactions in the multi-well micro plate, wherein the sensor system comprises one or more sensors selected from the group consisting of an absorbance sensor, a fluorescence sensor, and a luminescence sensor.

In another aspect, a non-transitory computer readable medium is disclosed having instructions stored thereon, wherein execution of the instructions by a processor, cause the processor to obtain one or more data sets associated with measurement of a multi-well micro plate, where each measurement is associated with a measured level of endotoxins in an acquired sample of inject-able drug product or water over time, wherein the data set comprises a current measured level for each well of the multi-well micro plate, wherein the multi-well micro plate comprises at least 96 wells; and singularly display, in a pane of a graphical user interface, from the obtained data set, a side-by-side graph comprising a plurality of visual elements, wherein each visual element of the plurality of visual elements is associated with a current measured level of each of the at least 96 wells of the multi-well micro plate, wherein each visual element of the plurality of visual elements comprises a vertically oriented bar that is configured to span data values ranging between a minimum and a maximum value, wherein each of the minimum value and maximum value are coincident with a first and second horizontal line, wherein the display further comprises a visual element comprising a third horizontal line at a measured value that indicates onset threshold for each of the at least 96 wells of the multi-well micro plate, and wherein the side-by-side graph of the at least 96 wells of the multi-well micro plate provides simultaneous comparison of speed of reaction in, or among group of wells of, the at least 96 wells of the multi-well micro plate to monitor testing of endotoxin in the acquired sample of inject-able drug product or water.

In some embodiments, the instructions when executed by the processor further cause the processor to control a sensor system configured to interrogate, and acquire measurement of, the at least 96 wells of the multi-well micro plate for measurement of the measured level of endotoxin reactions in the multi-well micro plate, wherein the sensor system comprises one or more sensors selected from the group consisting of an absorbance sensor, a fluorescence sensor, and a luminescence sensor.

Other systems, methods, features and/or advantages will be or may become apparent to one with skill in the art upon examination of the following drawings and detailed description. It is intended that all such additional systems, methods, features and/or advantages be included within this description and be protected by any accompanying claims in this application or any application that claims priority to this application.

BRIEF DESCRIPTION OF THE DRAWINGS

The accompanying drawings, which are incorporated in and constitute a part of this specification, illustrate embodiments and together with the description, serve to explain the principles of the methods and systems. The components in the drawings are not necessarily to scale relative to each other. Like reference numerals designate corresponding parts throughout the several views. The patent or application file contains at least one drawing executed in color. Copies of this patent or patent application publication with color drawing(s) will be provided by the Office upon request and payment of the necessary fee:

FIG. 1 is a block diagram of an exemplary system for analyzing a fluid sample for endotoxins;

Figure 2B:
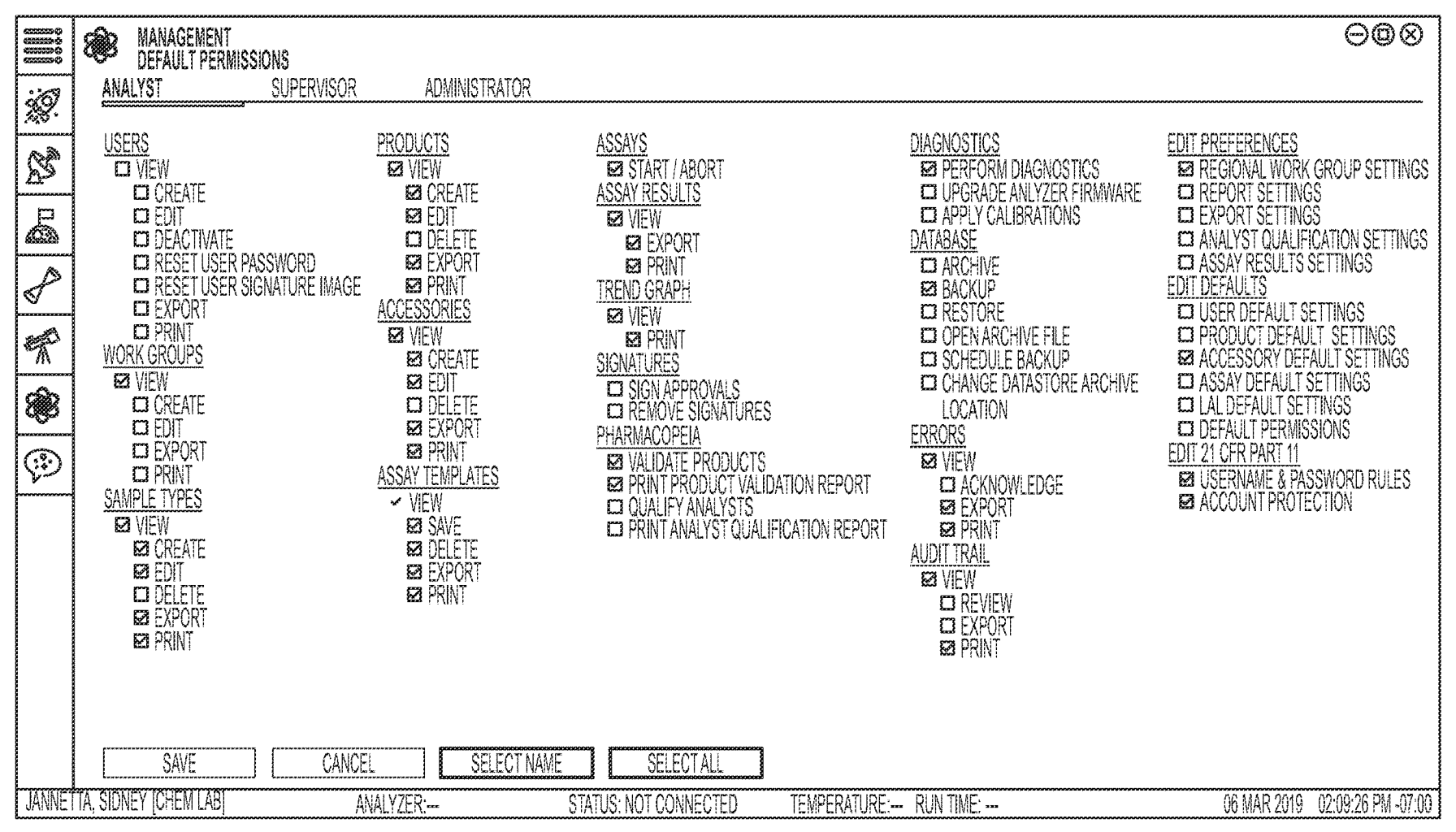
Figure 2C:
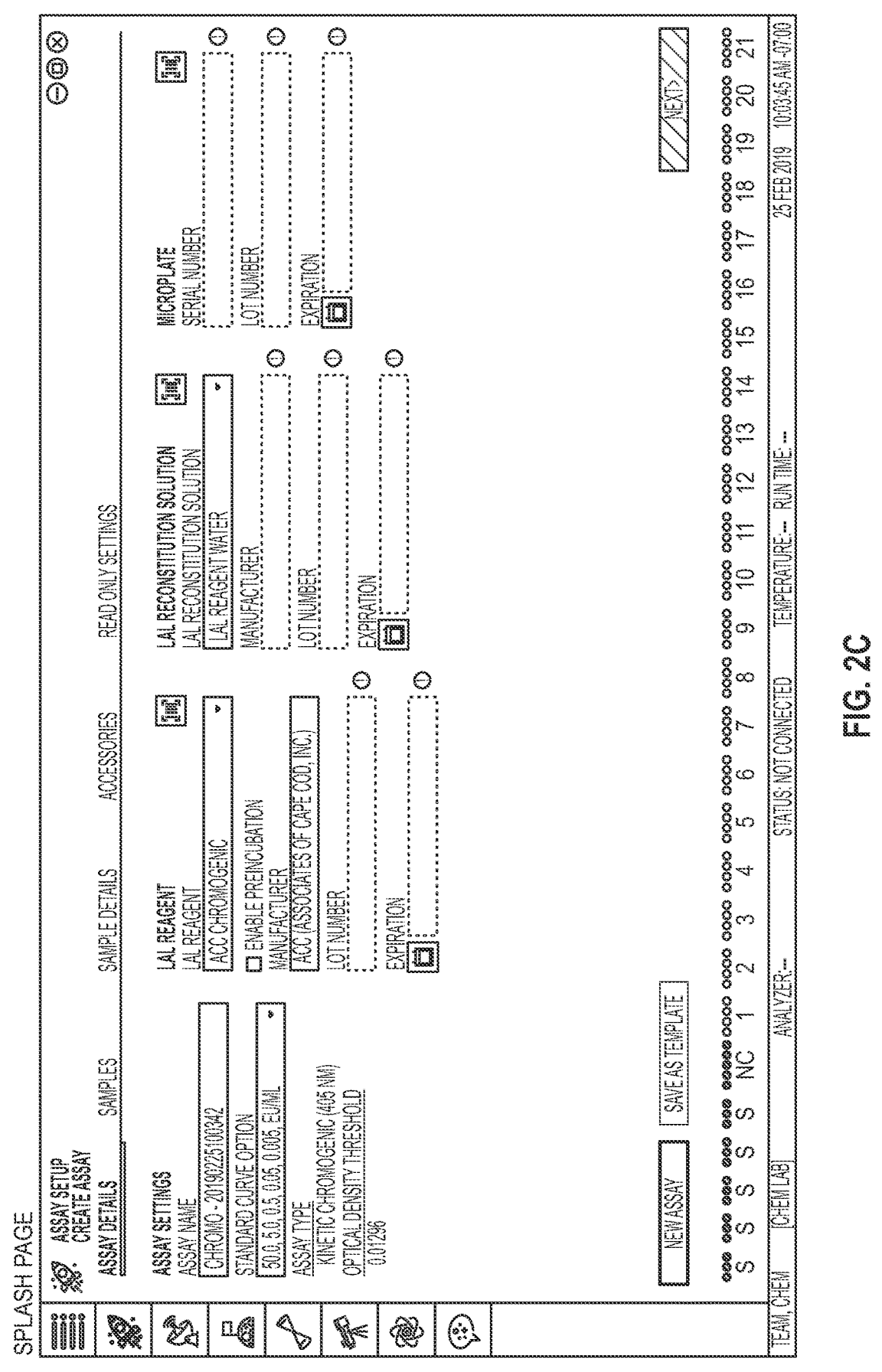
Figure 2D:
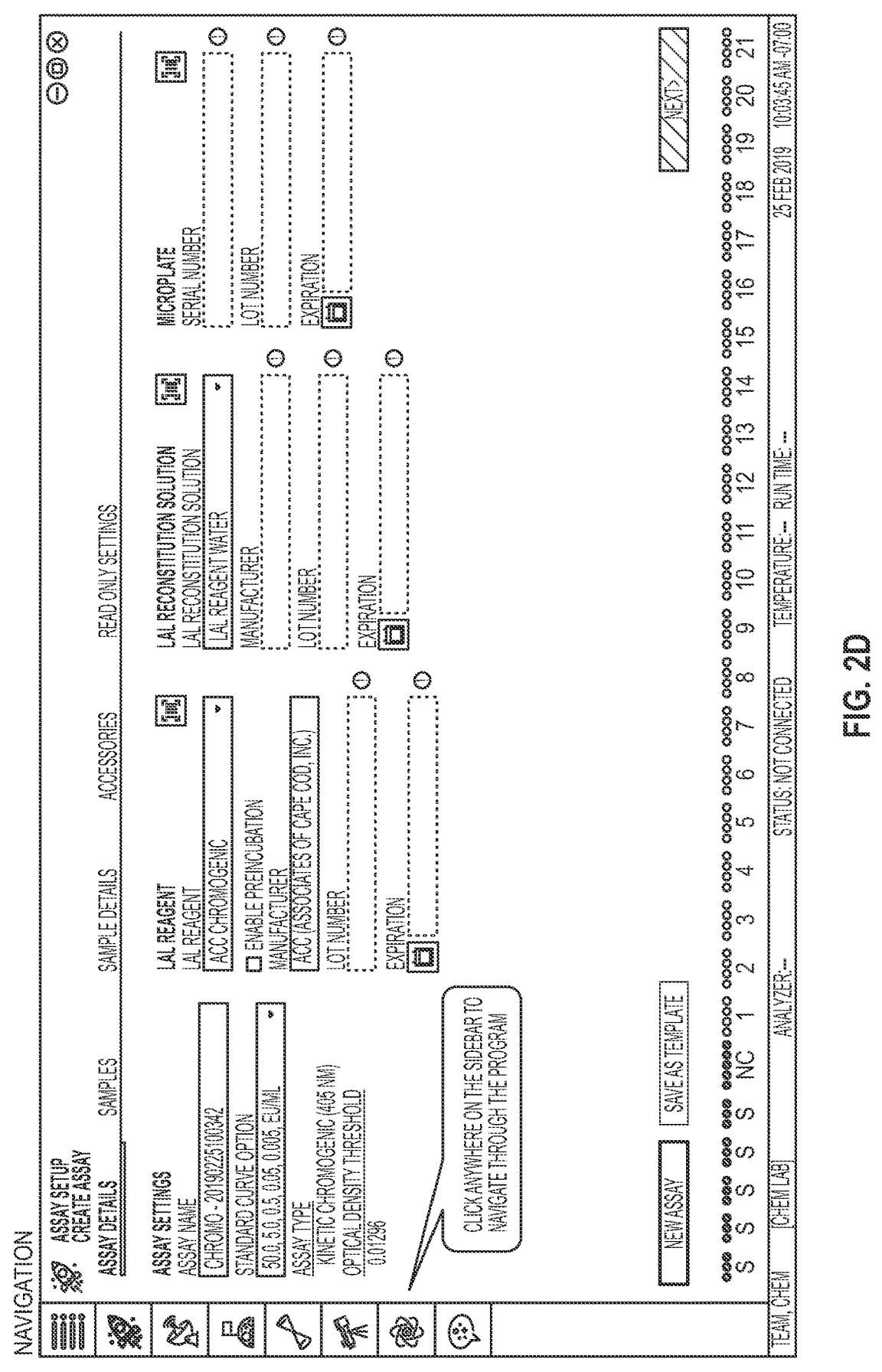
Figure 2E:
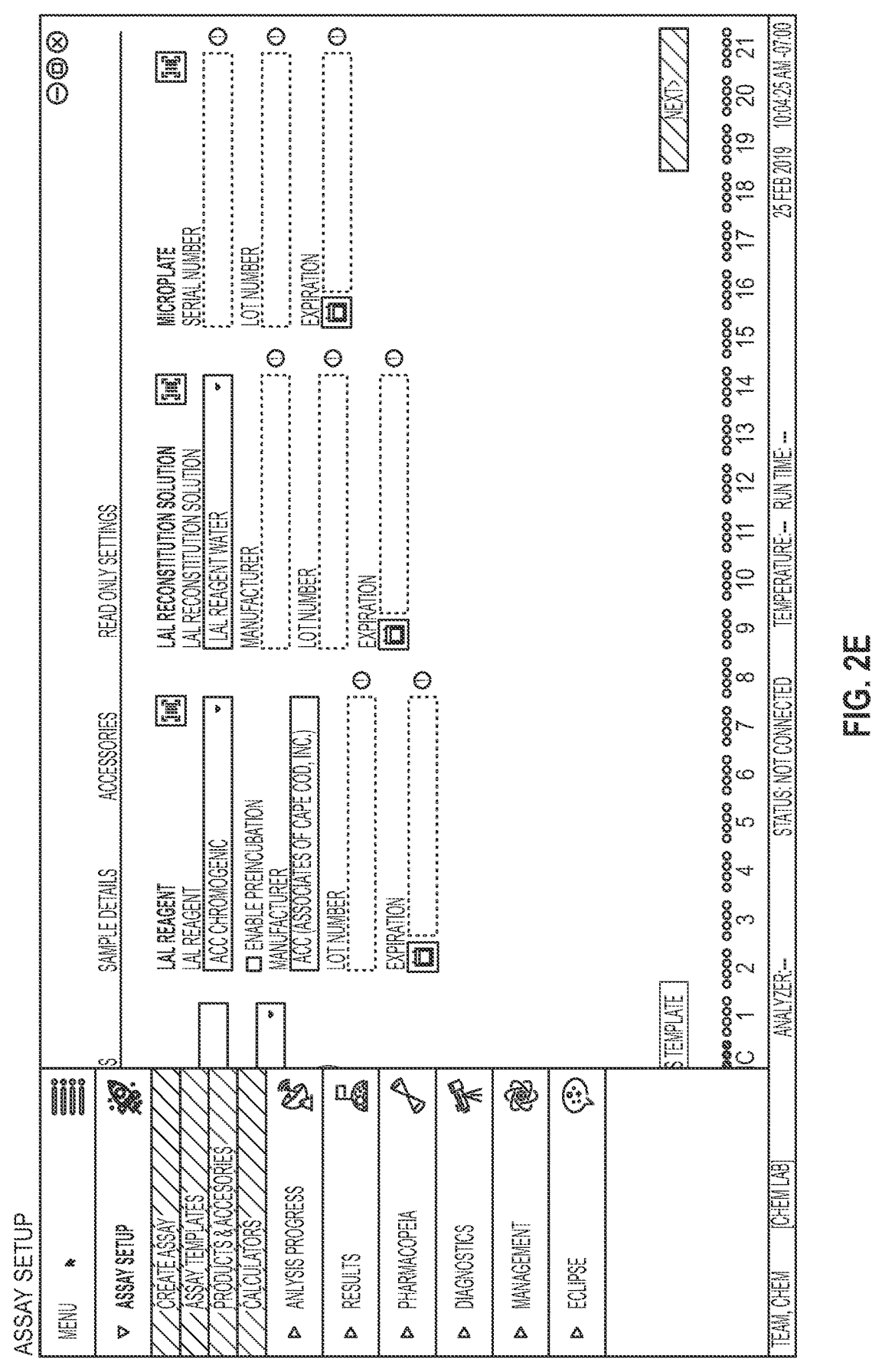
Figure 2F:
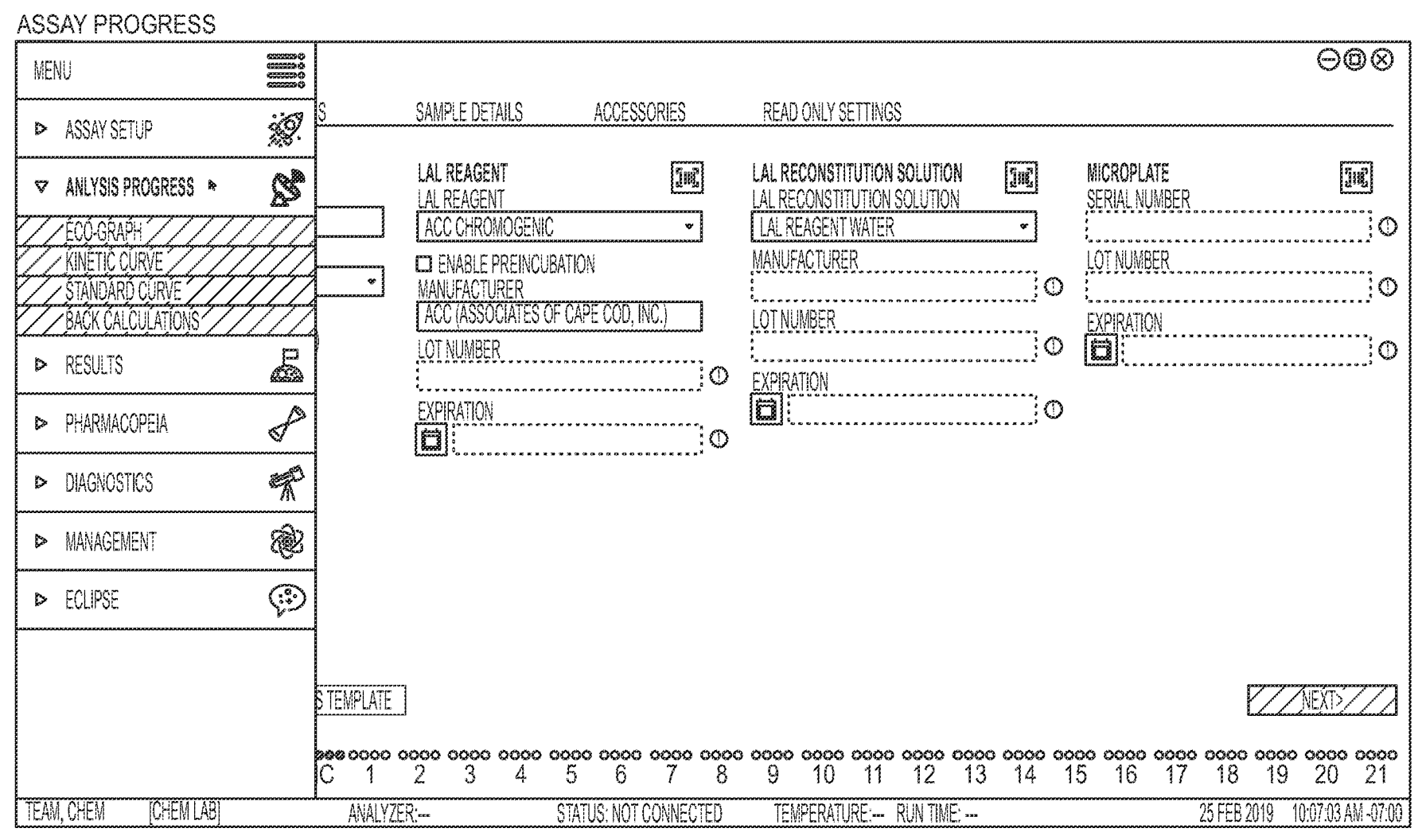
Figure 2G:
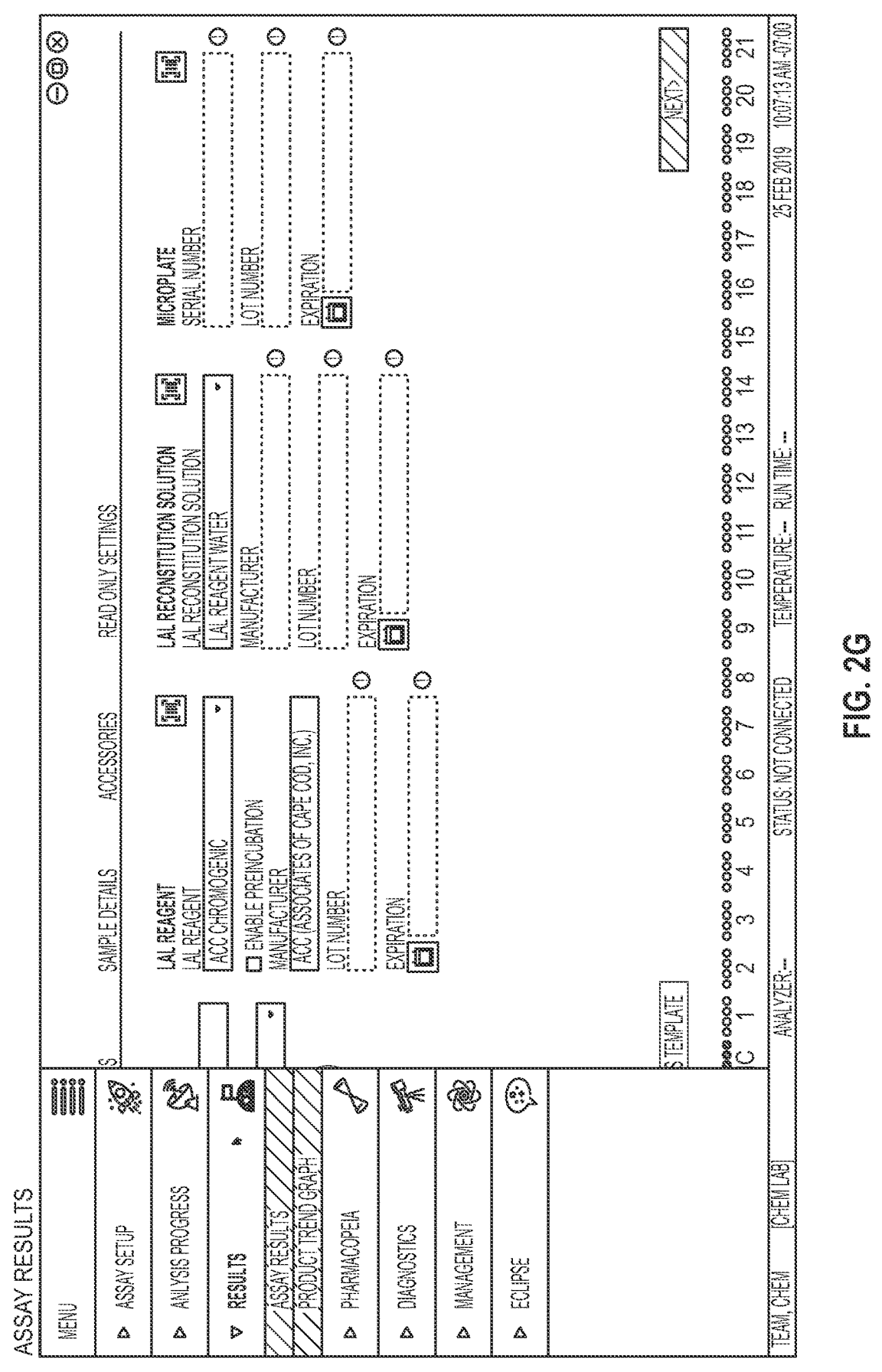
Figure 2H:
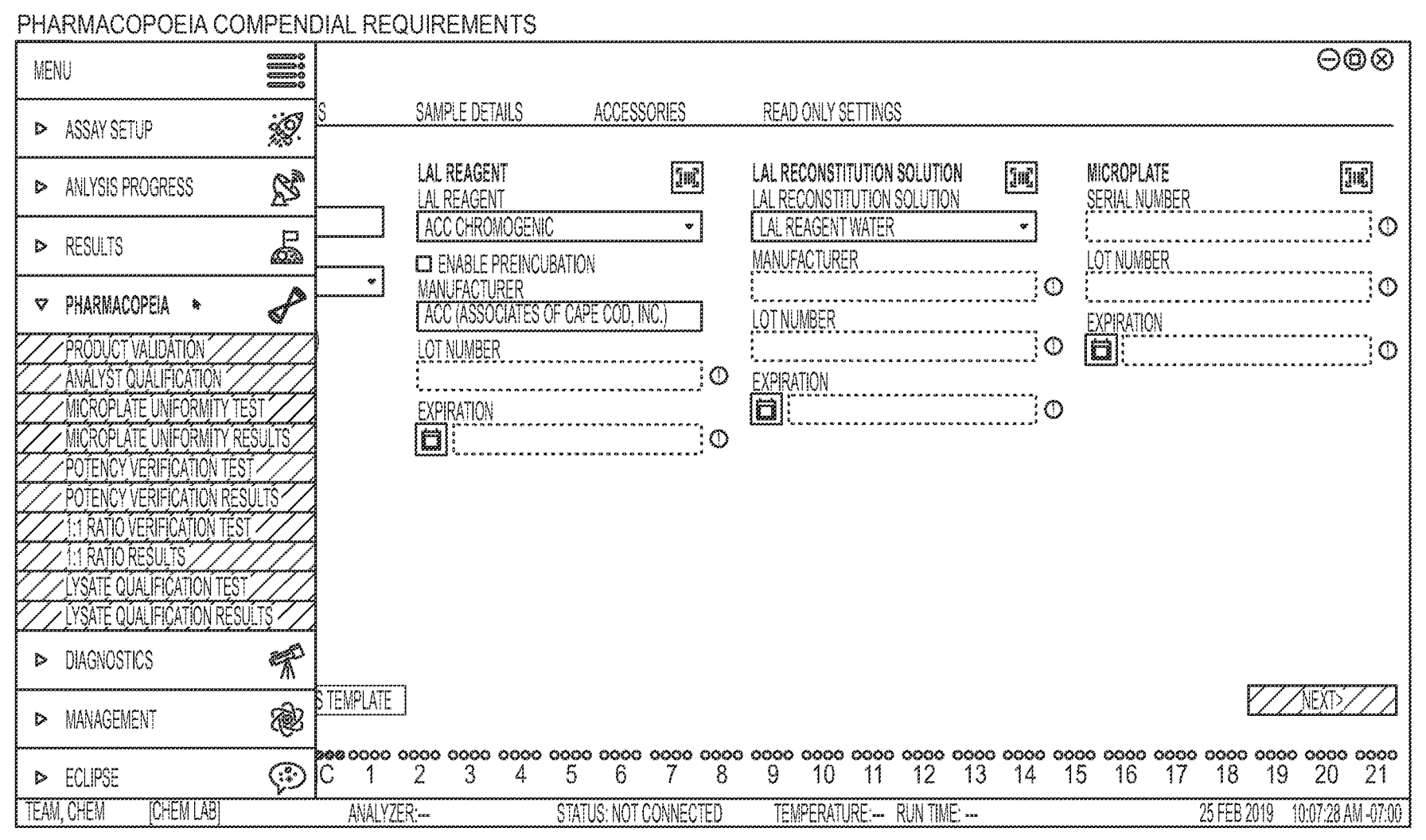
Figure 2J:
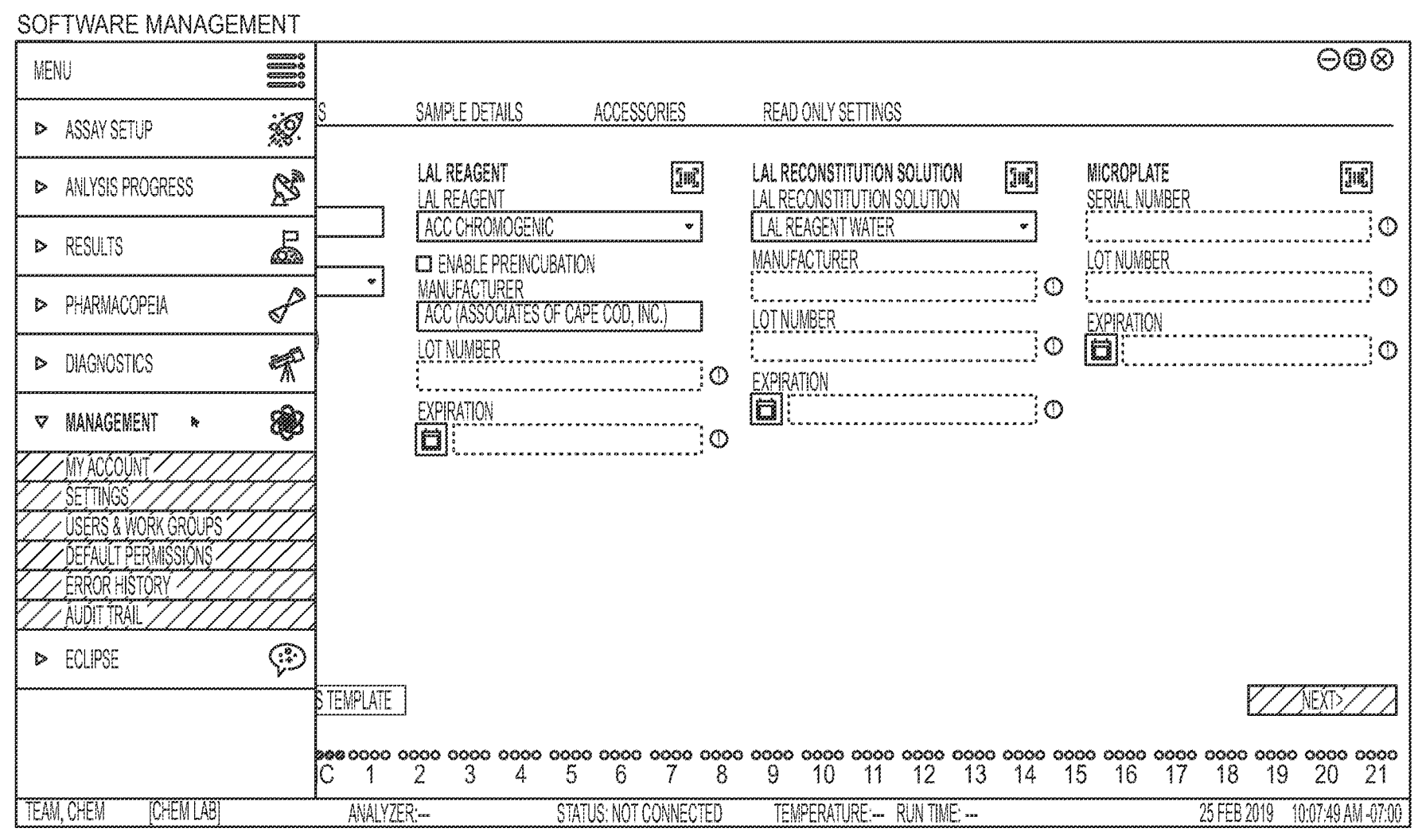
Figure 2K:
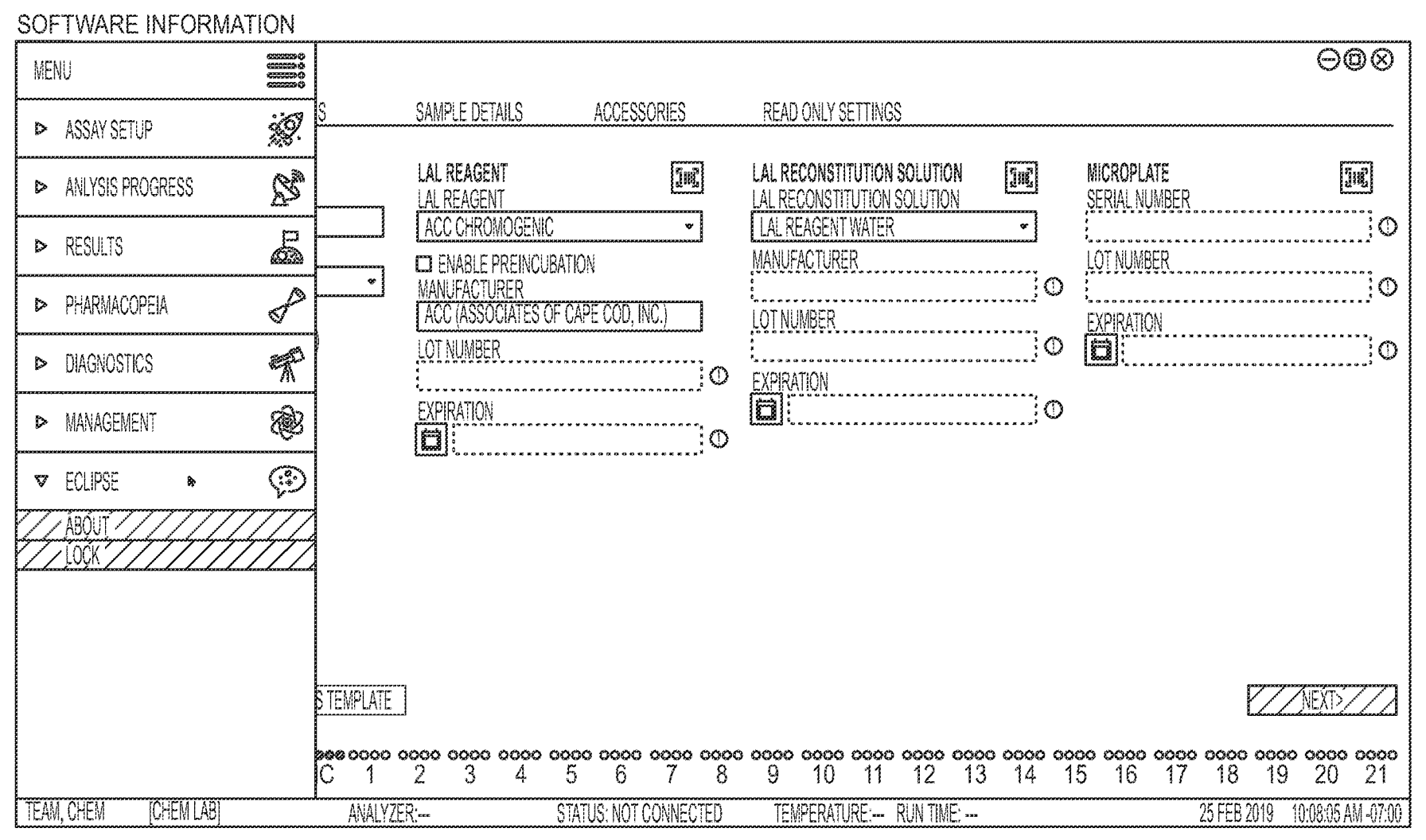

FIGS. 2A-2K are screen captures of exemplary graphical user interfaces (GUIs) of an embodiment of the analysis software described herein;

FIG. 14 illustrates an exemplary computer having a processor that can be used for executing the analysis software described herein.

DETAILED SPECIFICATION

Figure 2A:
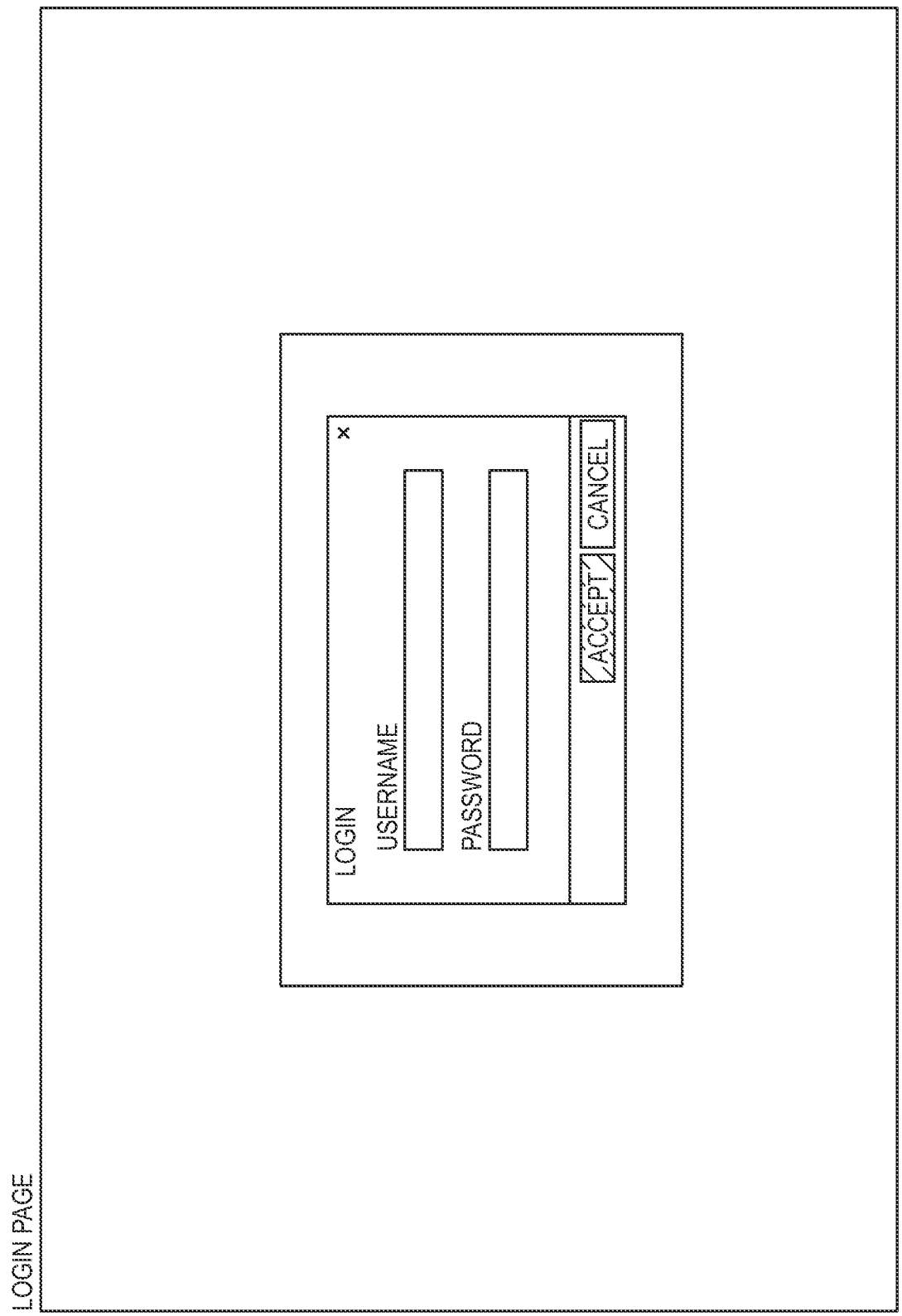

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes. The terms "optional" or "optionally" used herein mean that the subsequently described feature, event or circumstance may or may not occur, and that the description includes instances where said feature, event or circumstance occurs and instances where it does not.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

It is understood that throughout this specification the identifiers "first", "second", "third", "fourth", "fifth", "sixth", and such, are used solely to aid in distinguishing the various components and steps of the disclosed subject matter. The identifiers "first", "second", "third", "fourth", "fifth", "sixth", and such, are not intended to imply any particular order, sequence, amount, preference, or importance to the components or steps modified by these terms.

FIG. 1 is a block diagram of an exemplary system for performing endotoxin analysis of a fluid sample 102. In FIG. 1, an analyzer 104 receives a fluid sample 102. Non-limiting examples of analyzers that can be used include Sievers™ Total Organic Carbon (TOC) analyzers and instruments as available from SUEZ Water Technologies & Solutions (Boulder, CO). The analyzer 104 performs an analysis of the fluid sample 102 and provides raw data 106, which can be further analyzed to determine bacterial endotoxin concentrations in the sample 102 (a bacterial endotoxin test (BET)). Exemplary systems and methods for performing the analysis of the fluid sample 102 as shown and described in U.S. Pat. No. 9,678,079 issued Jun. 13, 2017, which is fully incorporated by reference.

The raw data 106 is provided to a data analysis processor 108 that analyzes the raw data 106 using analysis software 110. It is to be appreciated that the data analysis processor 108 may be integrated into and be a part of the analyzer 104, or it may be a separate processor such as a stand-alone computer or analytics device.

The analysis software 108 interpolates raw data 106 from the analyzer 104 to detect a change in optical density over time for the purposes of detecting endotoxin. Embodiments of the analysis software 108 may be used to analyze raw data from other types of analyzers, e.g., those that provide measurements based on change in optical properties (e.g., absorbance, luminance, fluorescence, etc.).

An embodiment of the analysis software 108 utilizes SQL server and can be installed as a standalone (database resides on the laboratory PC itself) or client/server (SQL database resides on a remote server with client application installed on the laboratory PC). The software application 108 is highly customizable and allows for each organization to assign user roles and permissions as per their quality management system. The program tracks products, accessories, analysts, eclipse microplate lot, LAL lot, assay performance (% CV, R-value, PPC recovery, etc.), and more for on-going trending.

Figure 3A:
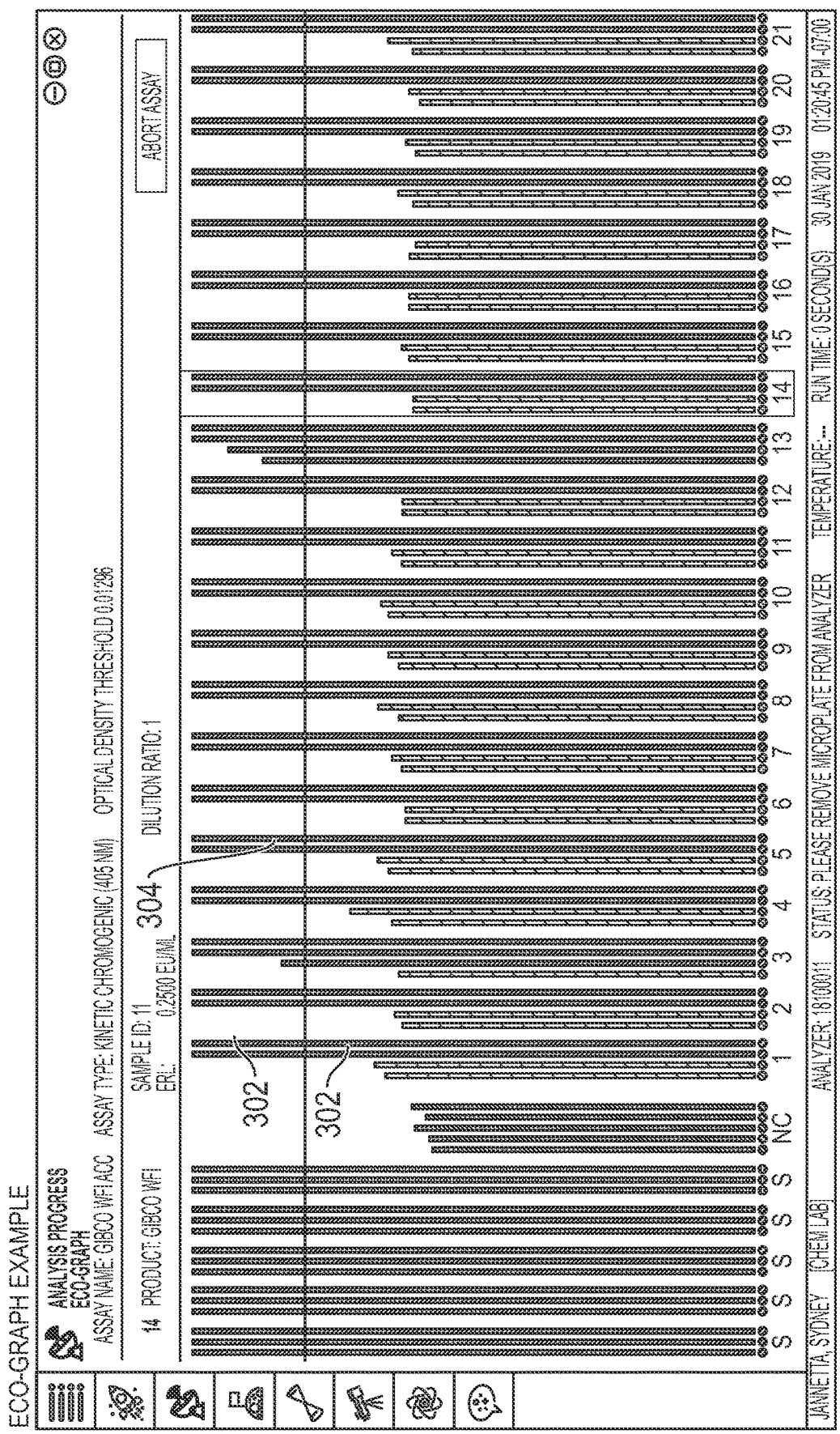
FIGS. 3A and 3B each illustrates a graphical user interface that comprise a visual representation, in the form of a vertically-oriented bar graph, of the kinetic reactions that occur when performing an endotoxin analysis using the analysis software described herein.
Figure 3B:
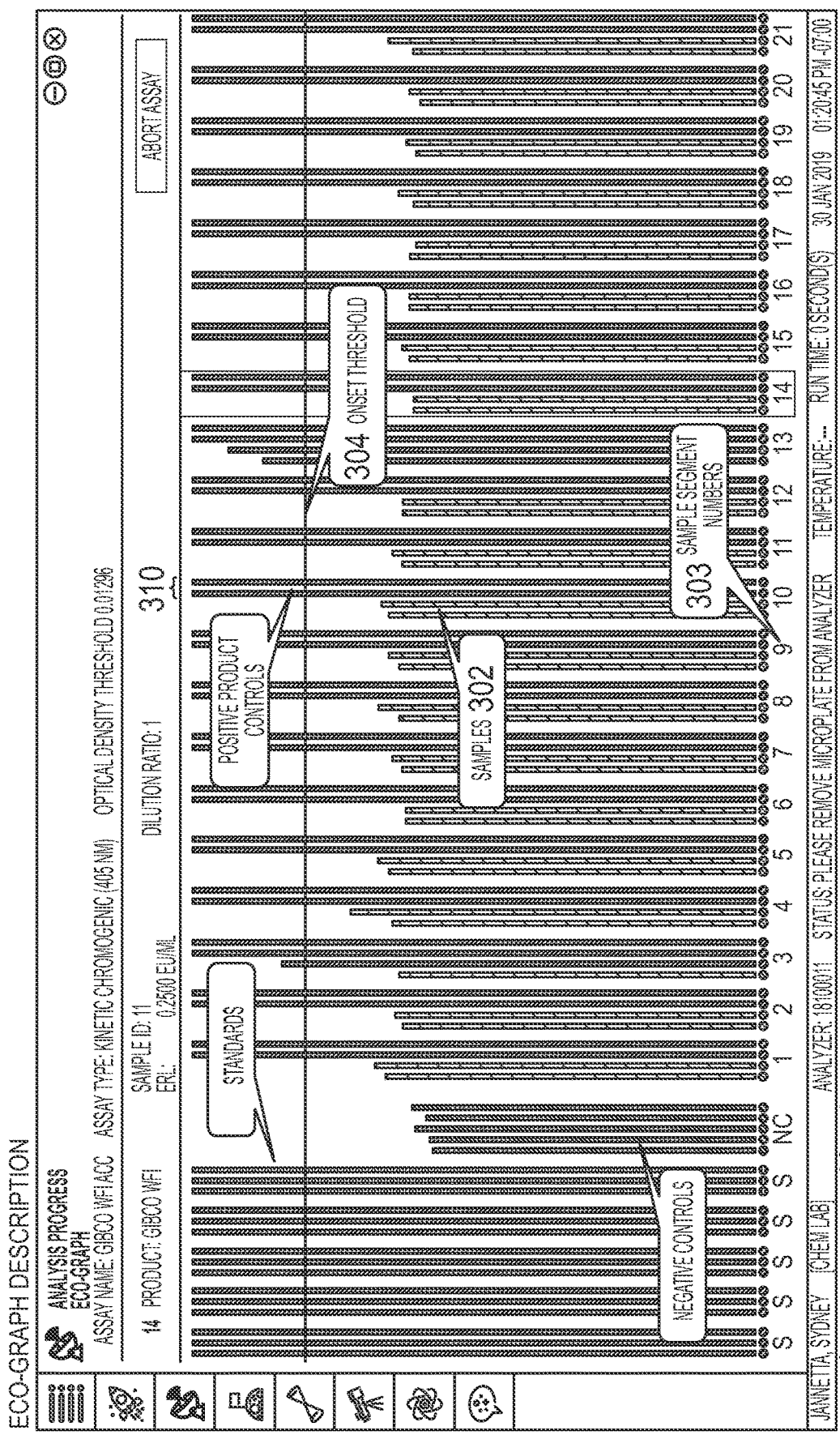

FIGS. 2A-2K are diagrams of exemplary graphical user interfaces (GUIs) of an embodiment of the analysis software described herein. As shown in FIGS. 2A-2K, the analysis software 108 includes a unique "Pharmacopeia" section within the Menu navigation—this section contains test setup and test results for those tests directly tied to regulatory requirements and/or validation and routine maintenance (for example; analyst qualification, 1:1 ratio verification, and lysate qualification). The "Diagnostics" section also allows customers to implement firmware upgrades or run either of the temperature verification or the optical verification tests. Upon log in, the navigation menu in the analysis software 108 can be minimized or enlarged, and any subcategory of the menu can be accessed quickly. Lastly, the analysis software 108 differentiates itself from conventional BET software by providing a colorful and descriptive GUI or report 112, as shown in FIGS. 3A and 3B and described below.

Endotoxin Reaction Visualization

During the endotoxin reaction (e.g., to testing reagents) in an assay, a useful information is the progress of the reaction in reaching the onset threshold (e.g., how quickly is the reaction reaching onset threshold; how long before the reaction reach onset threshold; and how is the reaction progressing with respect to related reactions of the same test group, etc.). An embodiment of the instant visualization generates a bar graph for each reaction chamber (test wells) to show progress of the measured reaction to the onset threshold. The measured reactions, e.g., of all of the wells, are concurrently presented to provide a simultaneous view of all statuses of the endotoxin reactions for a microplate test. The instant visualization facilitates visualization of various progress of onset threshold of endotoxin reactions for a given plate—e.g., progress of individual wells, progress of individual wells with respect to the group, progress of standard wells, etc.). For example, the instant visualization can facilitate the identification of wells having faster or slower reactions or whether reactions of a group of wells are aligned as expected.

Embodiments of the instant visualization may be used with analysis software to analyze and/or view raw data from various analyzers, including those that provide measurements based on change in optical properties (e.g., absorbance, luminance, fluorescence, etc.) for endotoxin reaction progress visualization.

Indeed, the GUI or report 112, as shown in FIGS. 3A and 3B, includes a graphical visualization 300, e.g., generated by the data analysis processor 108 executing the analysis software 108, having the form of a side-by-side vertically-oriented bar graph of the 104 kinetic reactions that occur when running, e.g., an Eclipse® microplate (SUEZ Water Technologies & Solutions, Boulder, CO), though microplates of different manufacture having optical wells are contemplated within the scope of embodiments described herein. As shown in FIGS. 3A and 3B, each vertical bar 302 of the side-by-side bar graph represents the endotoxin reaction progress (e.g., which can be associated with an optical density (OD) reading, change in optical properties, etc.) of each associated optical well of the microplate. Standard micro plates typically have 96 wells or more. The instant GUI 112 has a graphical visualization for 104 wells, though the disclosed visualization embodiments can be adapted for 96 wells or more.

Referring still to FIGS. 3A and 3B, optical wells of samples are identified by sample segment numbers 303 shown horizontally across the bottom of the GUI or report 112. The vertical bars 302 increase over time as the reaction between one or more testing reagents (e.g., Limulus Amoebocyte Lysate (LAL) or its synthetic substitutes such as recombinant Factor C (rFC), Limulus clotting factor C, Limulus clotting enzymes, etc.) and bacterial endotoxin takes place in each well. Indeed, the more endotoxin present in the optical well (whether related to samples, endotoxin standards, or positive product controls) the faster the reaction occurs with the testing reagent, and subsequently the faster the associated bars increase. The horizontal line 304 (labeled as "Onset threshold" 304) on the graphical visualization represents the threshold OD or Onset OD. The time at which any given reaction passes that threshold is referred to as the "onset time" or "reaction time". Vertical bars associated with endotoxin standards (306) and negative controls (308) are labeled, in some embodiments, in one color (e.g., red) in every assay prior to reaching onset threshold while the vertical bars representing samples 302 can be labeled with a different color (e.g., blue) prior to reaching onset threshold. Once the vertical bar 302 reaches the onset threshold (e.g., line 304), in some embodiments, and as shown in FIGS. 3A and 3B, the GUI is configured to adjust the color of the bar 302 of the graphical visualization 300 (e.g., from red or blue to green) to indicate that a given well has reached onset threshold state.

The GUI or report 112 provides users a comprehensive and global view of progress of kinetic reactions occurring in all wells of an exemplary microplate (e.g., 96-well microplate, 104-well micro-plate, etc.).

Figure 4A:
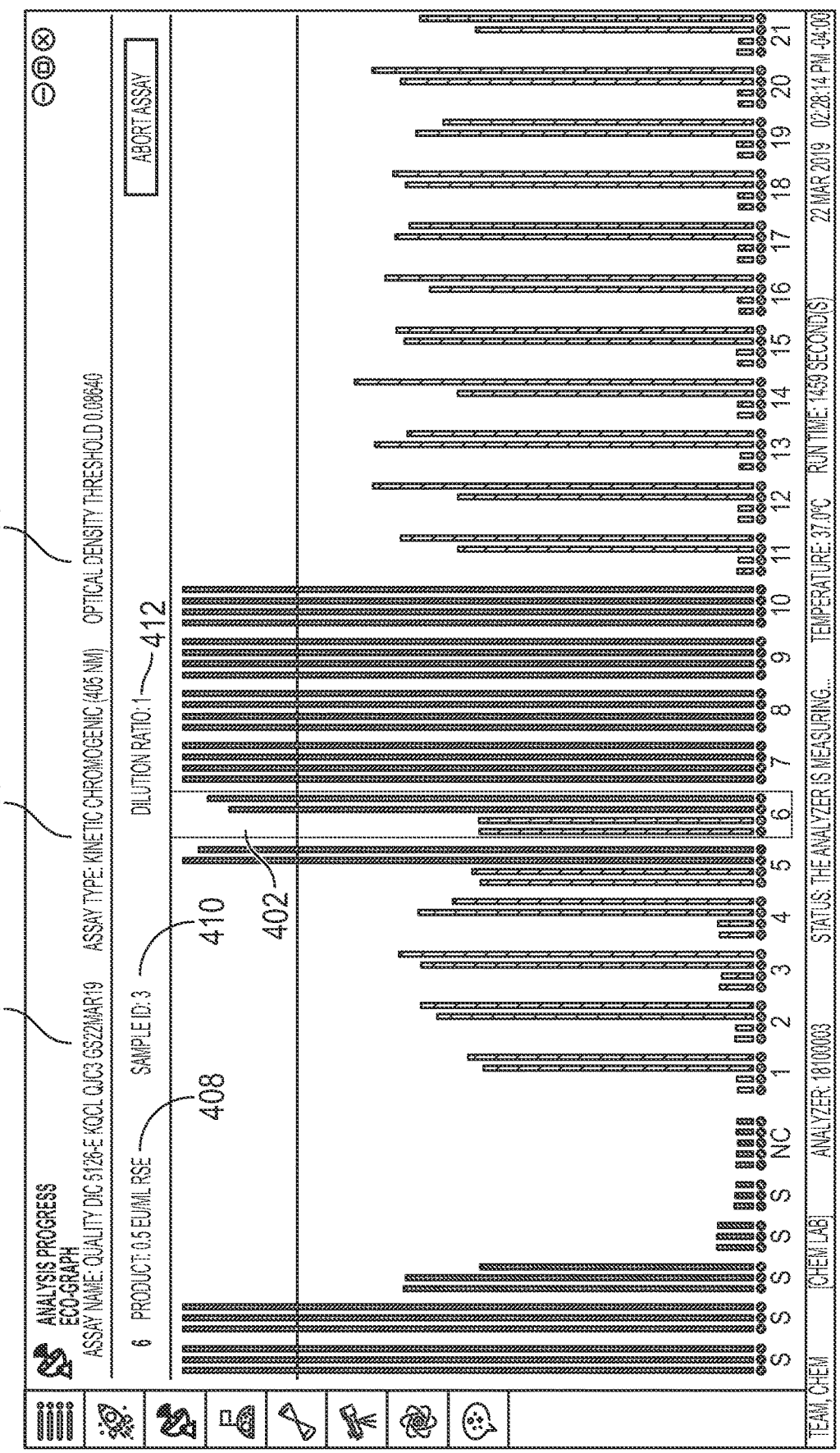
FIGS. 4A, 4B, and 4C each shows how reaction rate, progress of reaction, and relative progress of reaction can be viewed from the instant visualization, in accordance with an illustrative embodiment.
Figure 4B:
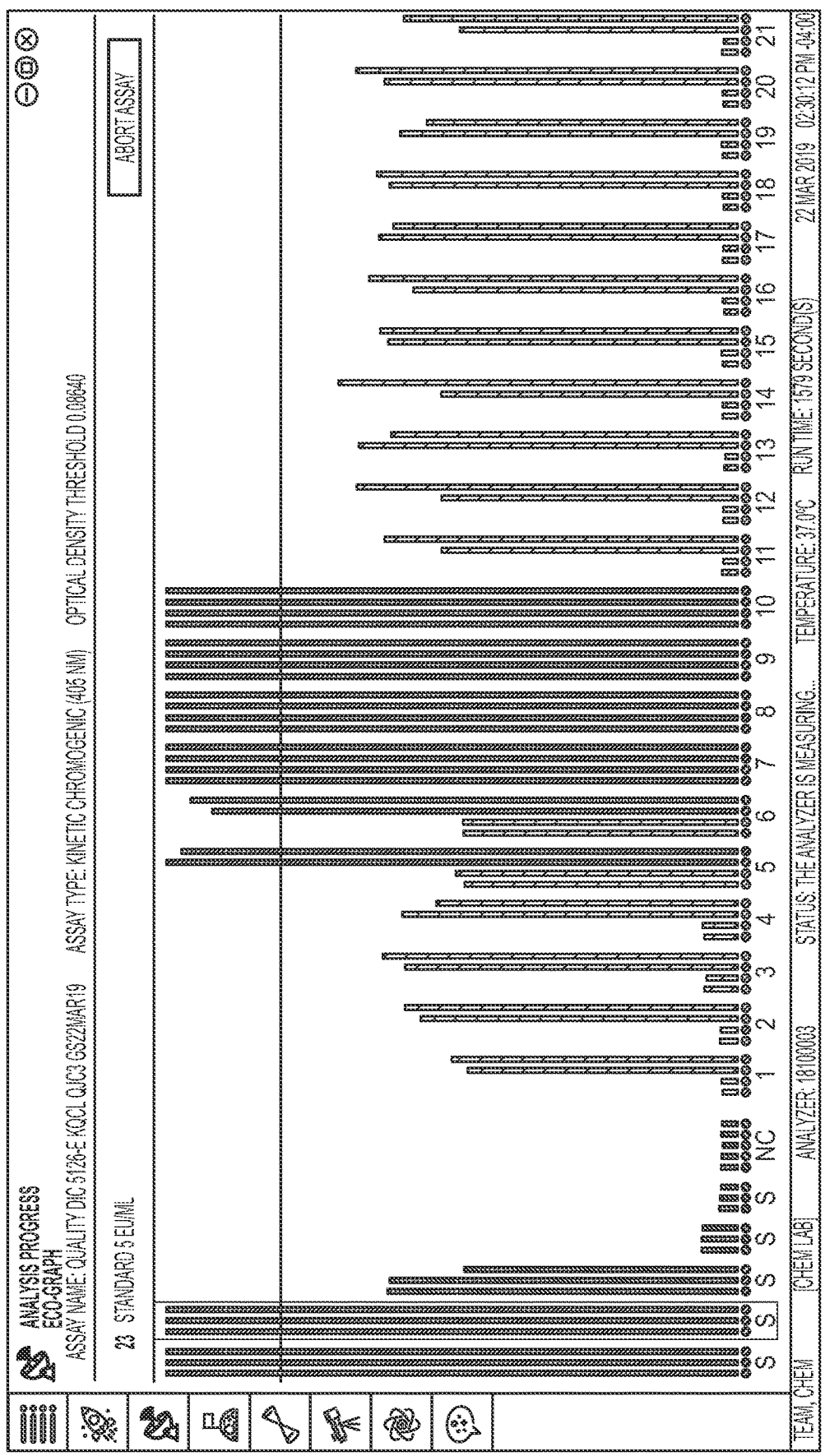
Figure 4C:
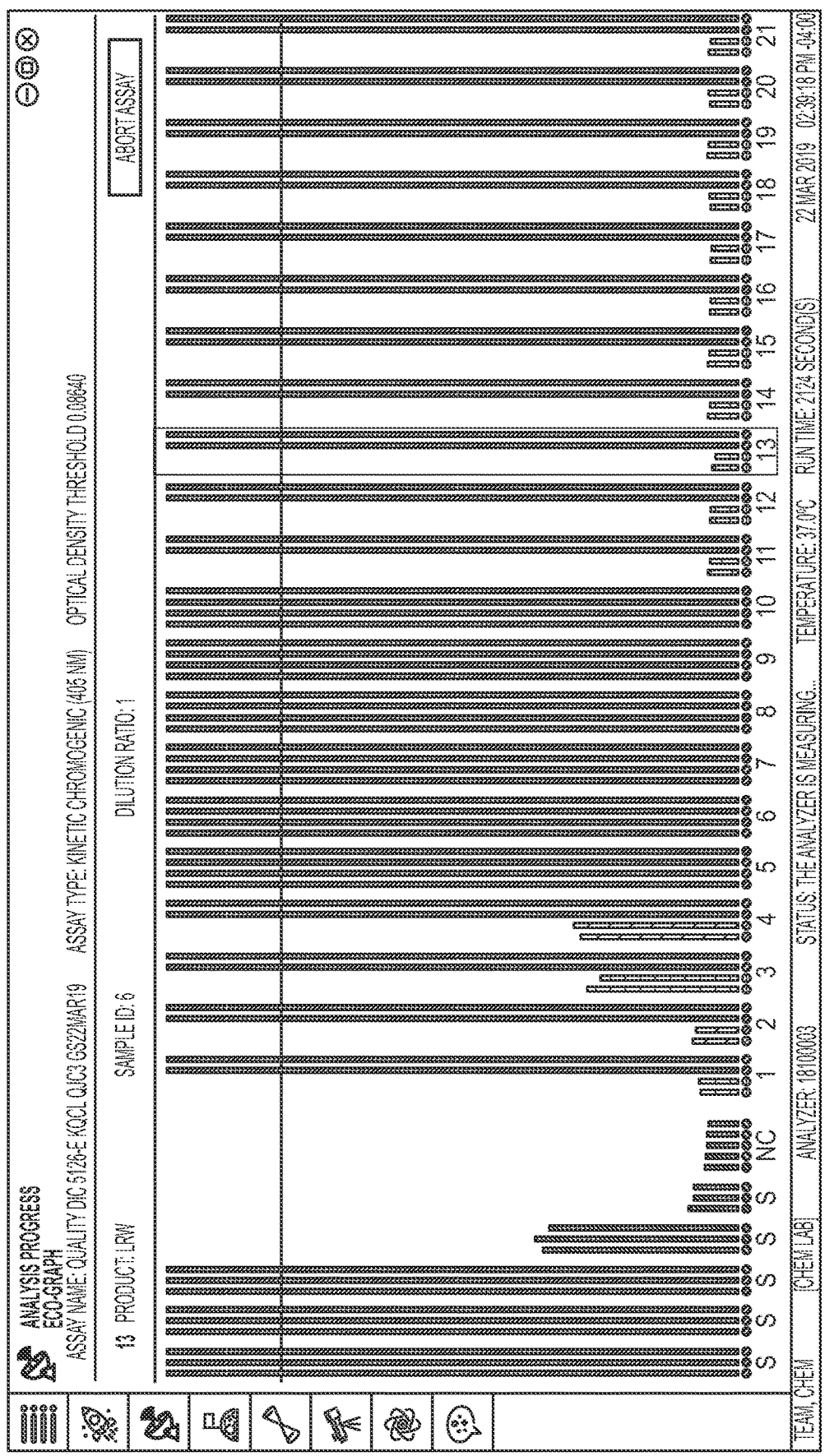

FIGS. 4A, 4B, and 4C each shows how reaction rate, progress of reaction, and relative progress of reaction can be viewed from the instant visualization, in accordance with an illustrative embodiment. In FIGS. 4A, 4B, and 4C, a visualization of the GUI 112 is provided at three different time instances for a same test. In FIG. 4A, visualization shows a snapshot of the test at runtime 1459 seconds; FIG. 4B shows a snapshot of the test at runtime 1579 seconds; and FIG. 4C shows a snapshot of the test at runtime 2124 seconds. As can be observed in FIGS. 4A and 4B, the standard wells are denoted in red and transitions to darker red (as the measurement approaches the onset threshold) and then transitions to green upon passing the threshold. Similarly, the test wells are denoted in blue and transition to darker blue (as the measurement approaches the onset threshold) and then transitions to green upon passing the threshold. And, as can be observed between FIGS. 4A and 4B, the vertical bars of certain wells transitions from red and blue to dark red and dark blue as the measured levels approaches the onset threshold. FIG. 4C shows the vertical bars of these wells transitioning to green upon passing the onset threshold line.

As indicated above, the higher endotoxin concentrations in the standard curve should react faster, and with the dynamic view a user is able to quickly identify a possible error in the standard curve (for example; the 5.0-EU/mL standard is reacting faster than the 50-EU/mL standard) or negative controls 308 and, if allowable, potentially abort the assay to expedite the retesting process due to an invalid assay. Furthermore, positive product controls (PPCs) 310 are product samples with a known amount of endotoxin added to them (often referred to as "spiked" or "product spikes"), and this is done with an endotoxin concentration in the middle of the standard curve range (for example; 0.5 EU/mL). Alternatively, positive product controls 310 may be calculated as a difference between the endotoxin concentration in PPC and the endotoxin concentration in the sample and the difference divided by an actual endotoxin concentration of the 0.5 EU/mL standard. In other embodiment, rather than dividing by the actual calculated value in each and every assay, the positive product controls 310 is calculated as a difference between the endotoxin concentration in PPC and the endotoxin concentration in sample and the difference is divided by a constant nominal 0.5 concentration. With the functionality of the shown GUI, an end user can observe the reaction rate, progress of reaction, and relative progress of reaction, of all sample PPCs (e.g., 21 sample PPCs) while simultaneously observing the reaction rate, progress of reaction, and relative progress of reaction, of the endotoxin standard at the same concentration (0.5 EU/mL, for example). With this comprehensive and global perspective, an analyst or technician performing the test can quickly identify whether sample PPCs are properly behaving to recover the required 50-200% of the endotoxin added. If an analyst or technician suspects that a sample will not pass they are able to quickly act to prepare next steps and actions in accordance with their quality management system (QMS).

Figure 5A:
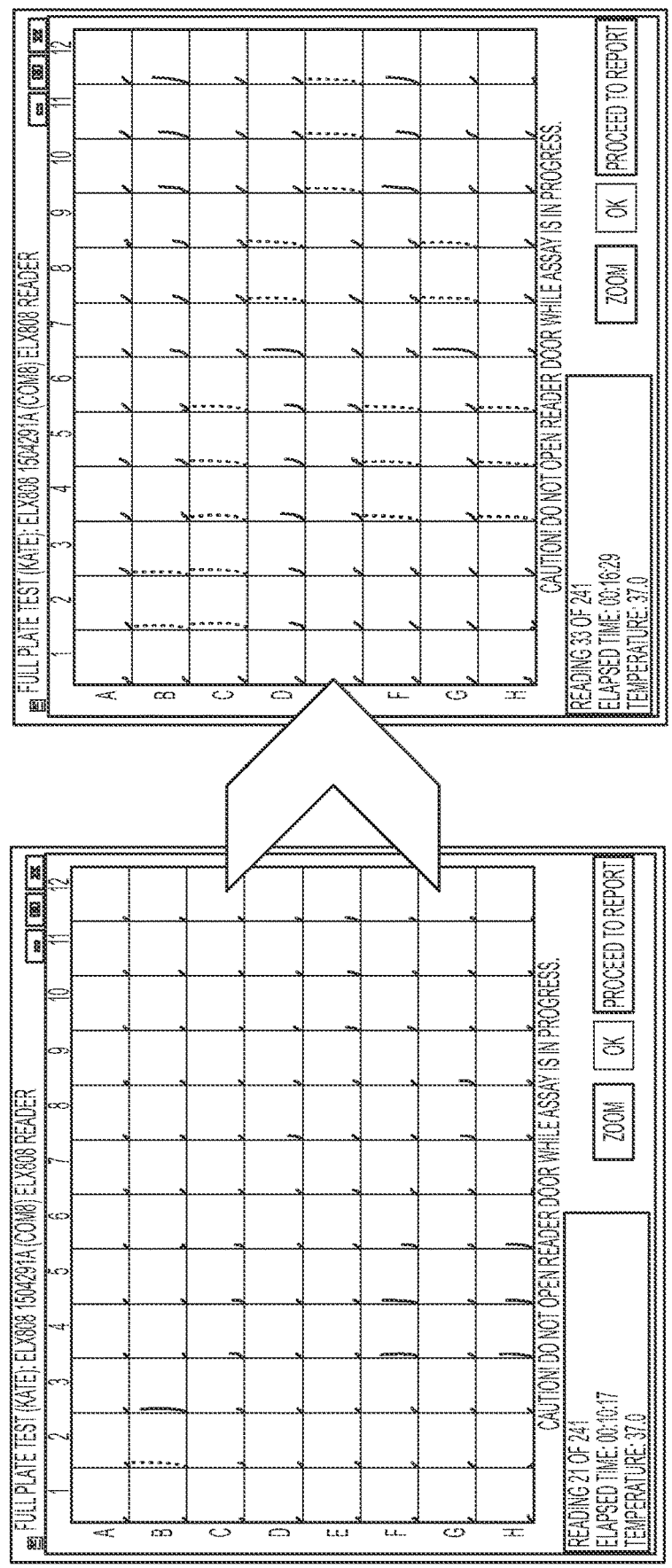
FIGS. 5A and 5B are examples of commercially available visualization of LAL test for a 96 well microplate.
Figure 5B:
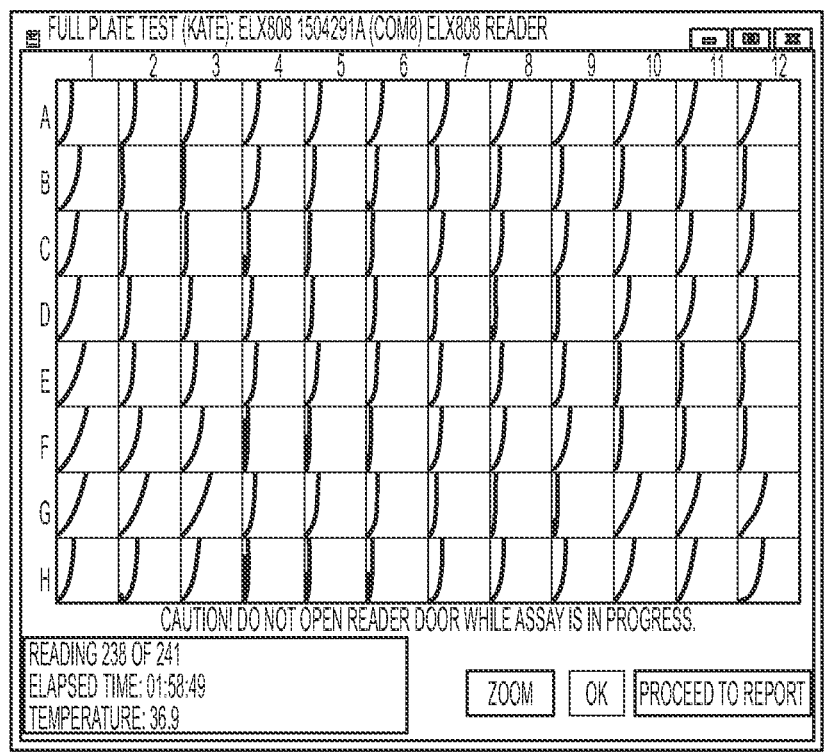

Currently, software applications for LAL test, and the like, display kinetic reaction curves over a period of reaction time of endotoxin in samples. In some embodiments, these software show the results in a matrix form, which does not provide the same quick and comprehensive information on endotoxin reaction rate, progress of endotoxin reaction, and relative progress of endotoxin reaction. FIG. 5A is an example visualization of the progress of kinetic test in a LAL test for a 96 well microplate. FIG. 5B is an example visualization of the same once the test is completed.

Endotoxin measurements in inject-able drug product or water are typically performed in a 96-well micro plate. Existing systems generally displays the measured levels (e.g., absorbance level) in forms of graphs (e.g., FIGS. 5A and 5B), which are difficult to assess or compare the reaction speed of the different wells. Further, these graphs does not facilitate the identification of unexpected reactions (e.g., whether a well is reacting too slowly or too quickly or whether a well is reacting consistently (i.e., aligned with) with others in the same group). In contrast, the side-by-side vertically-oriented bar graph can facilitate such identification more readily and more intuitively.

Figure 6A:
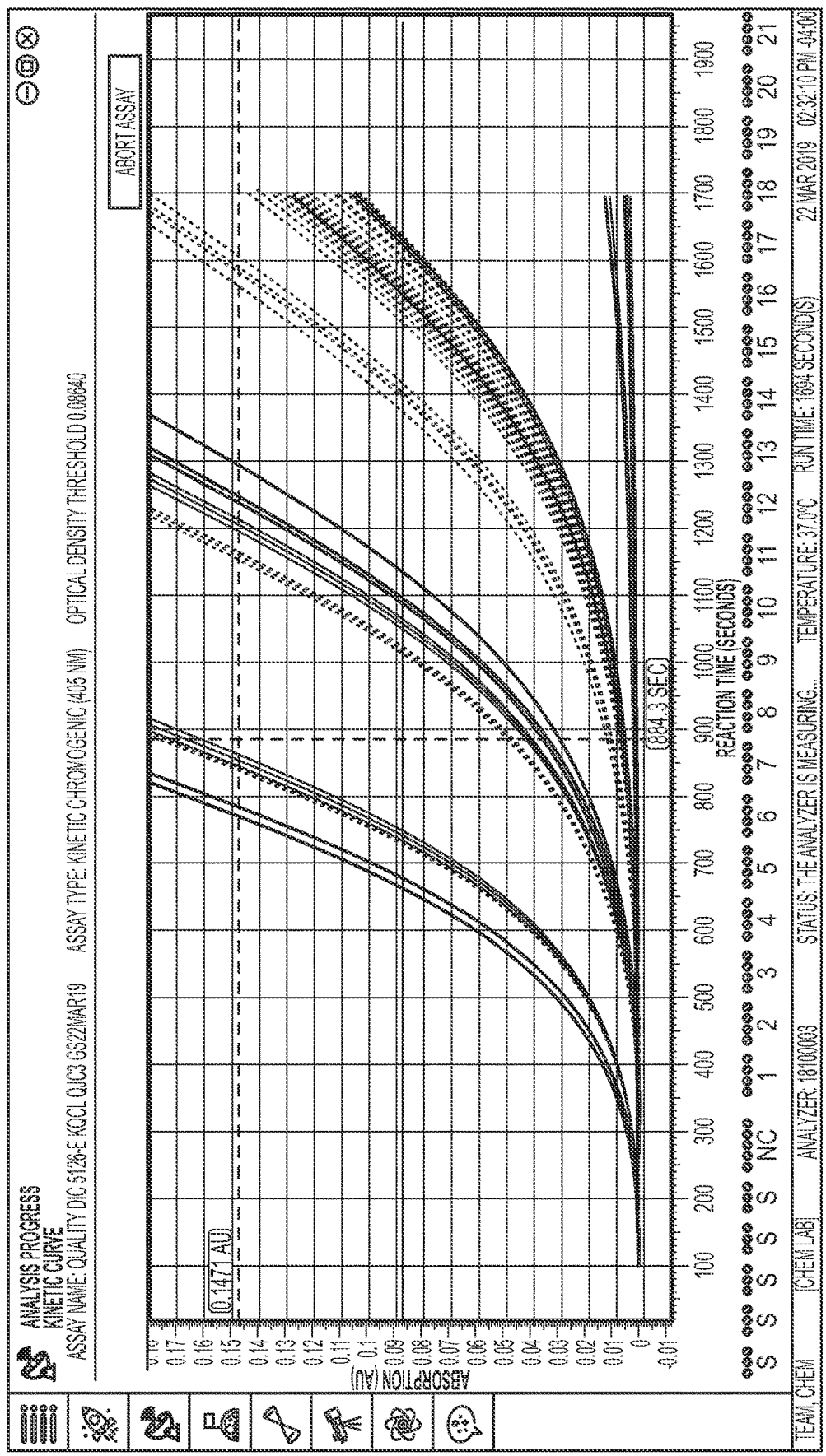
FIG. 6A shows a time-series kinetic reaction plot of a 104-well microplate that is arranged to provide more intuitive review of the assessment of progress of the LAL test.
Figure 6B:
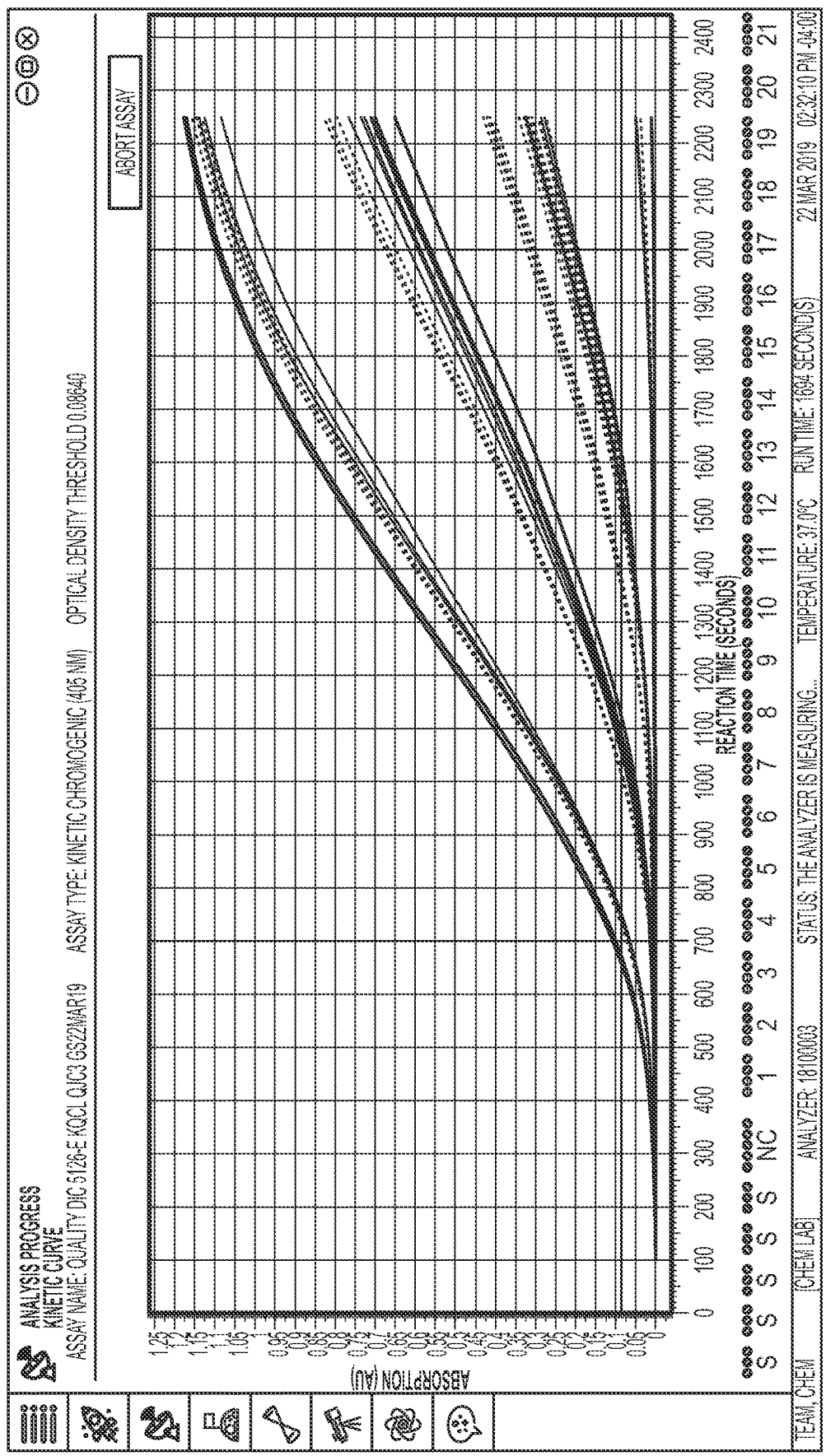
FIGS. 6B and 6C show the same at different viewing scale level.
Figure 6C:
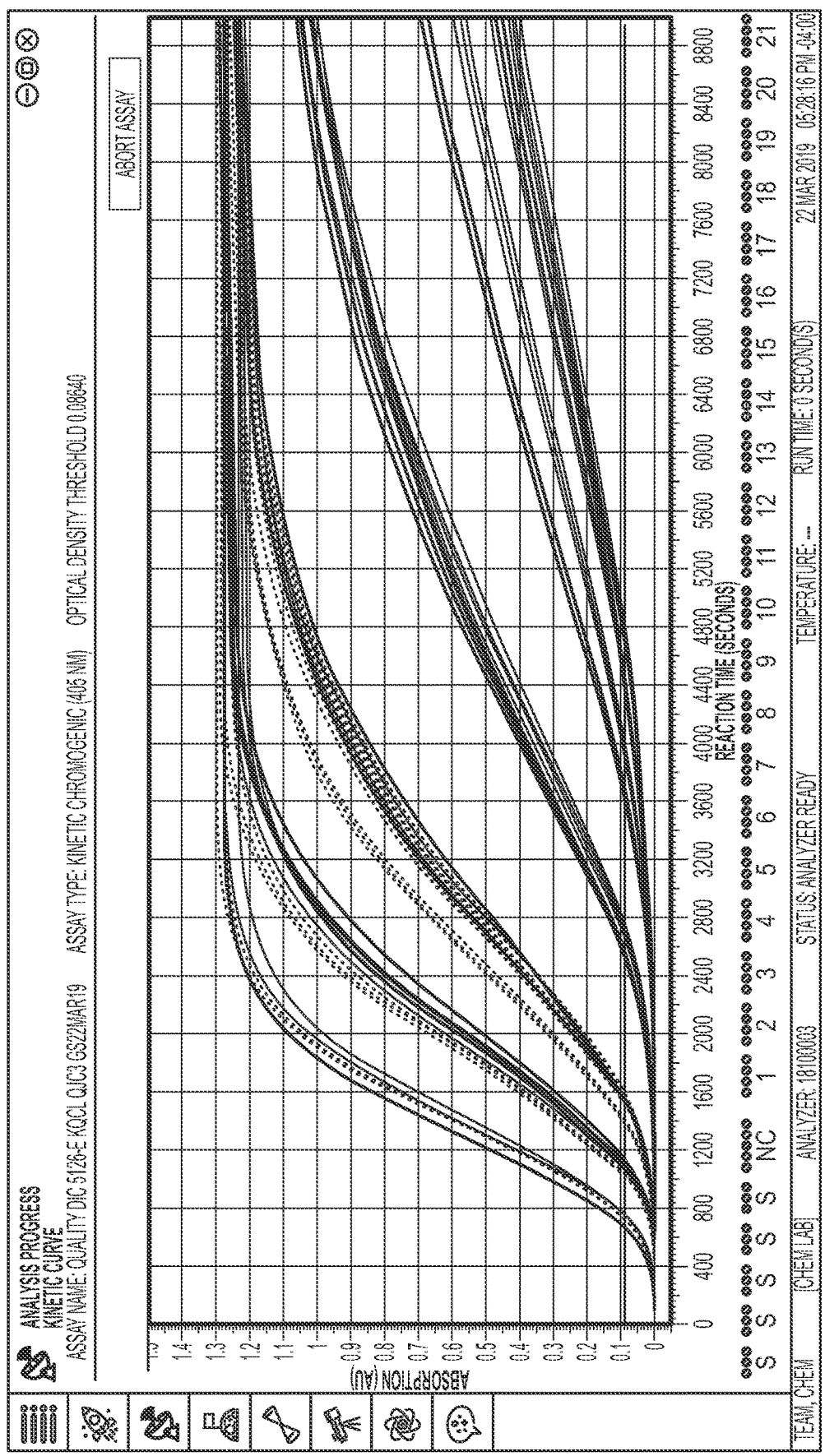

In another aspect, the microplate may be arranged, e.g., in certain groupings, to provide more intuitive view of assessing progress of the LAL test. FIG. 6A shows a time-series kinetic reaction plot of a 104-well microplate that is arranged to provide more intuitive review of the assessment of progress of the LAL test. FIGS. 6B and 6C show the same at different viewing scale level. As shown, the vertical axis are scaled to accommodate the samples being measured. Further, the x-axis is scaled for HD displays (more resolution).

In another aspect, the instant visualization can provide detailed information for a given well upon a selection of a well (e.g., via a cursor or keyboard). FIG. 4A shows detailed information about sample (402) such as assay name (404), assay type (406), optical density threshold (408), product sample identifier (409), and dilution ratio (410).

In another aspect, the instant visualization comprising side-by-side vertically-oriented bar graph may be used to view other parameters associated with the measurement or analysis. In some embodiments, the instant visualization is used to view measured values (e.g. change in optical properties, e.g., absorbance, fluorescence, luminescence, among others disclosed herein) of each wells in the microplate in a side-by-side vertically-oriented manner In some embodiments, the instant visualization is used to view determined onset time values of each wells in the microplate in a side-by-side vertically-oriented manner In some embodiments, the instant visualization is used to view measured endotoxin concentration values of each wells in the microplate in a side-by-side vertically-oriented manner In some embodiments, the instant visualization is used to view measured PPC recovery values of each wells in the microplate in a side-by-side vertically-oriented manner In some embodiments, the instant visualization is used to view assessed matrix effect values of each wells in the microplate in a side-by-side vertically-oriented manner.

FIGS. 7, 8, 9, 10, 11, 12, 13 each shows an example view of example parameters of wells, or group of wells, in a microplate that can be displayed in a side-by-side vertically-oriented manner, in accordance with an embodiment.

Figure 7:
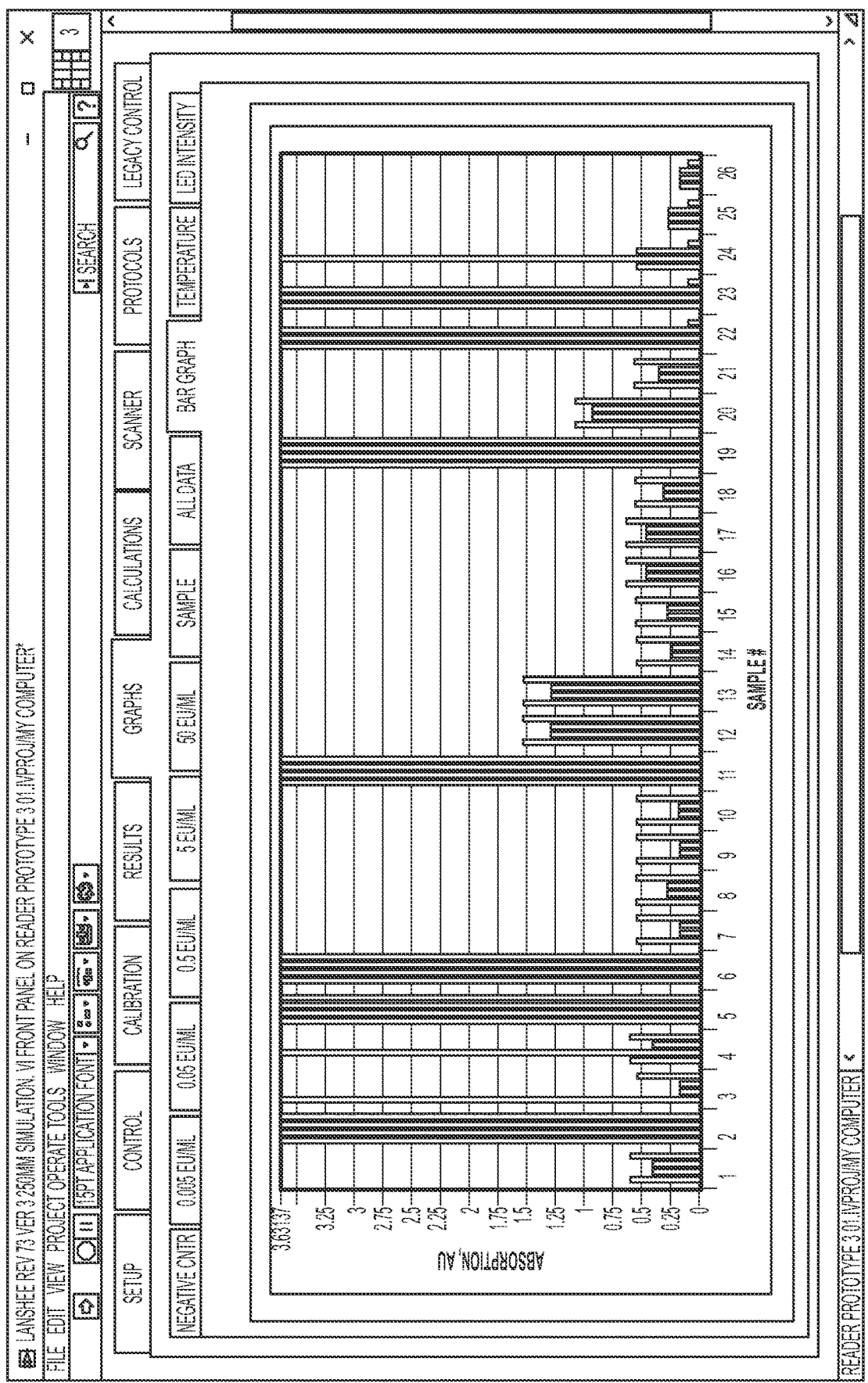
FIGS. 7, 8, 9, 10, 11, 12, 13 each shows an example view of example parameters of wells, or group of wells, in a microplate that can be displayed in a side-by-side vertically-oriented manner, in accordance with an embodiment.
Figure 8:
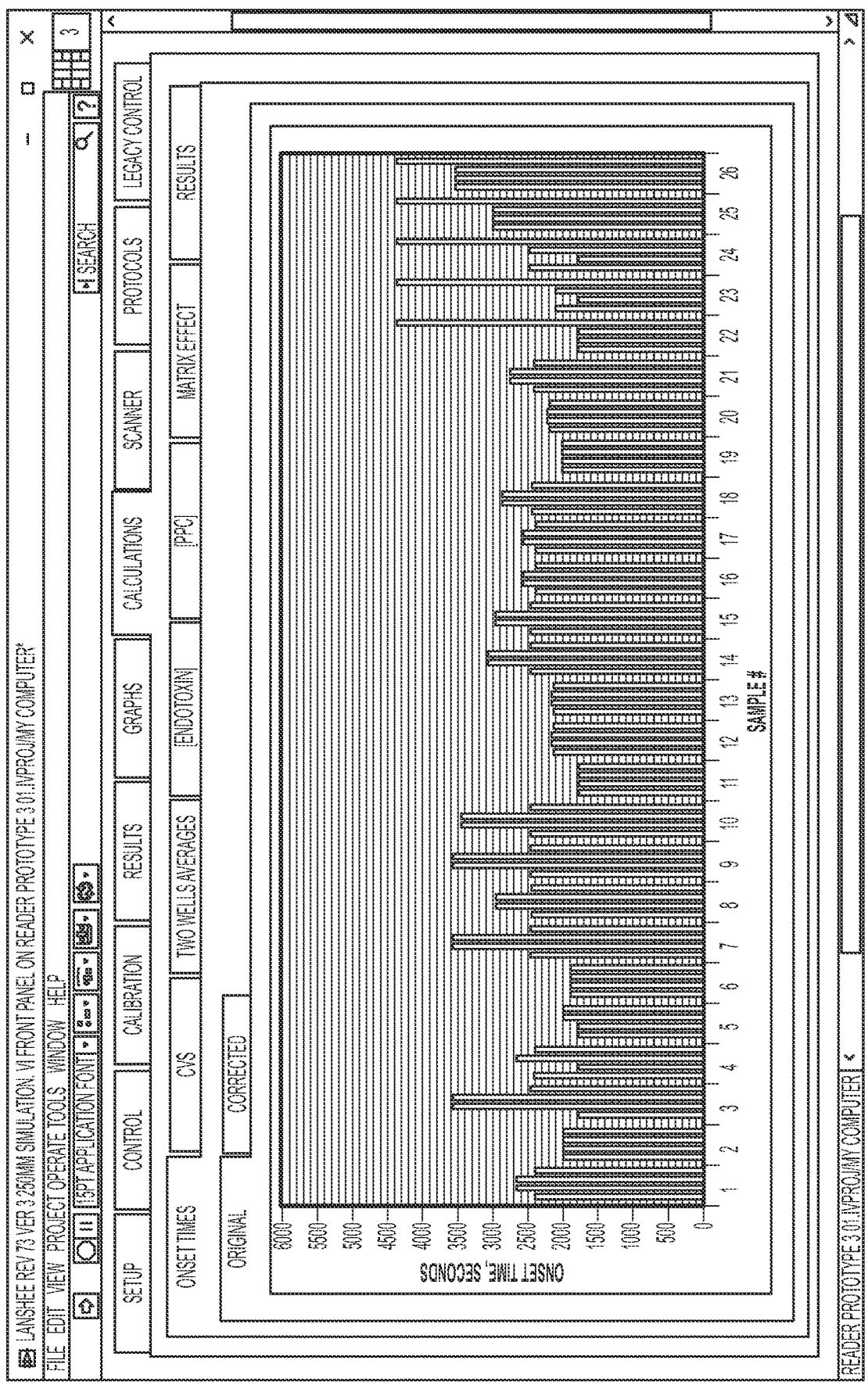
Figure 9:
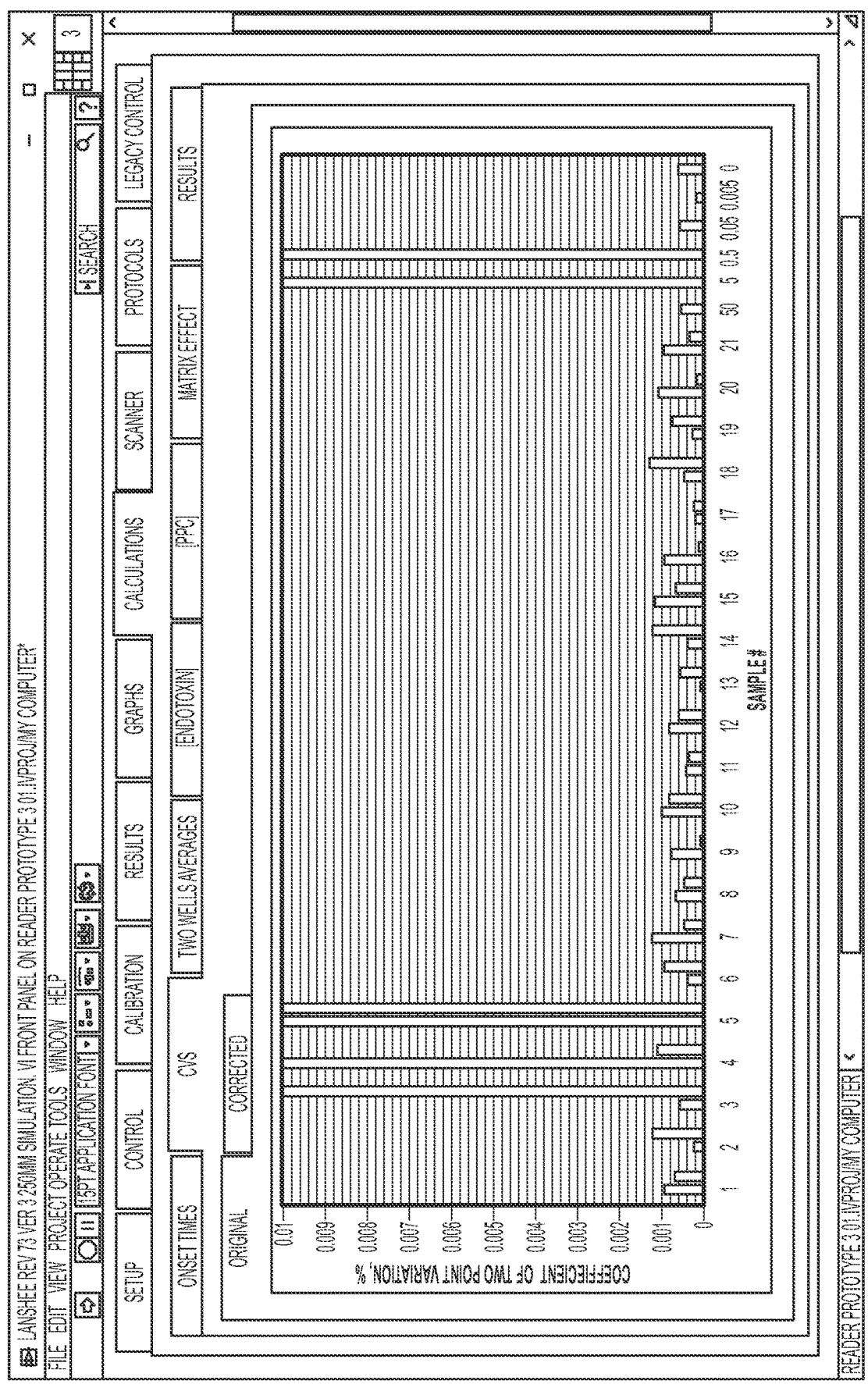
Figure 10:
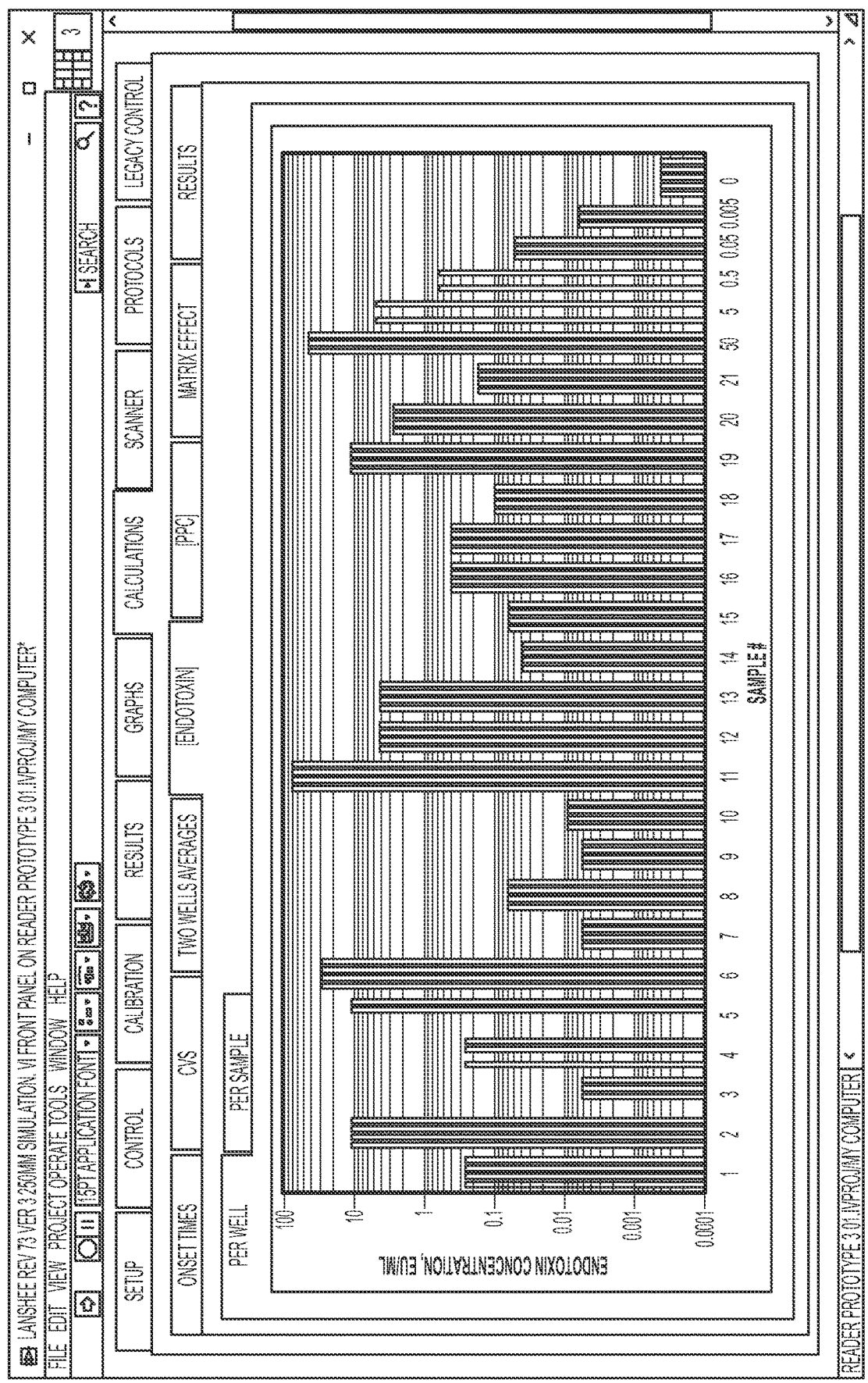
Figure 11:
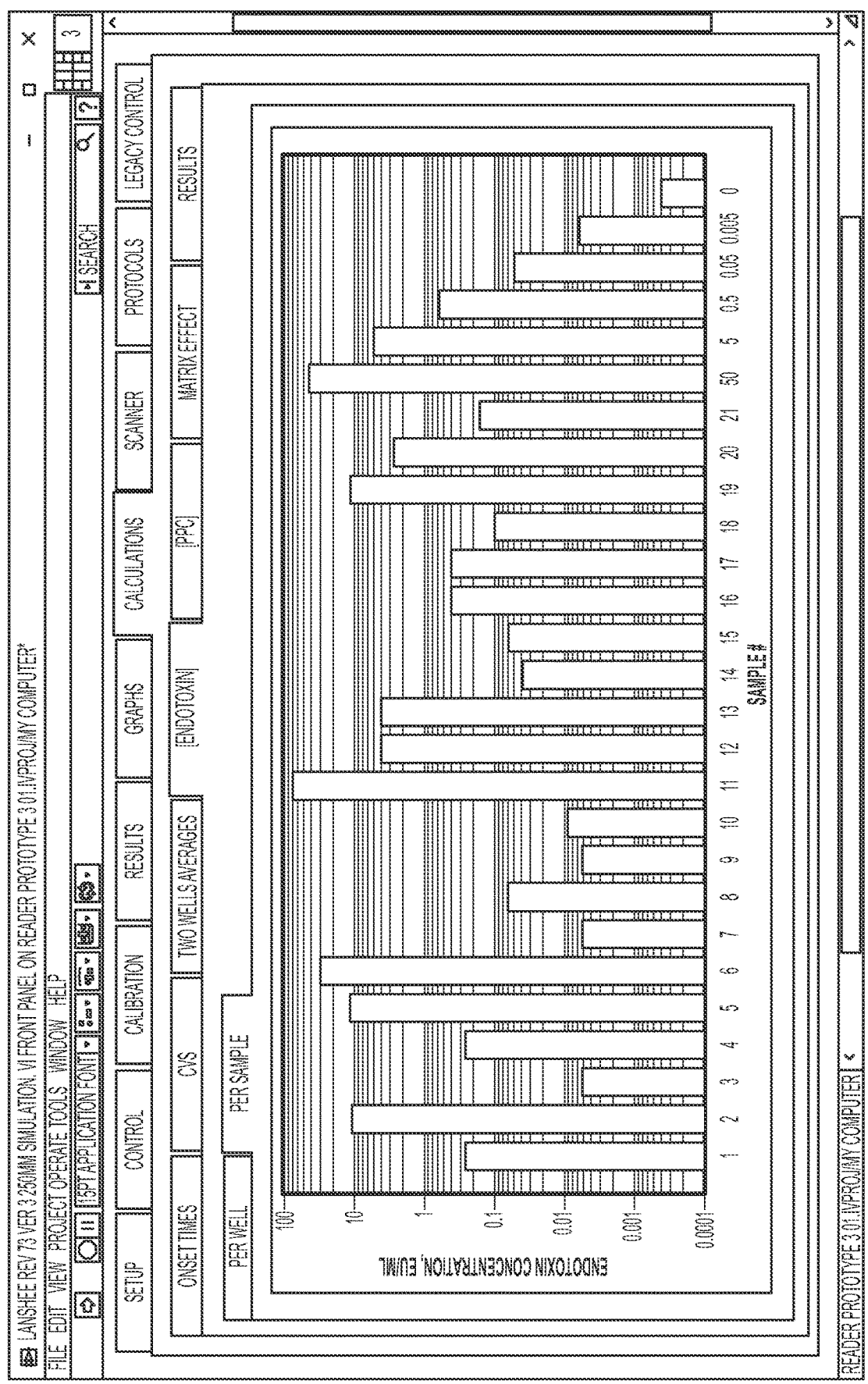
Figure 12:
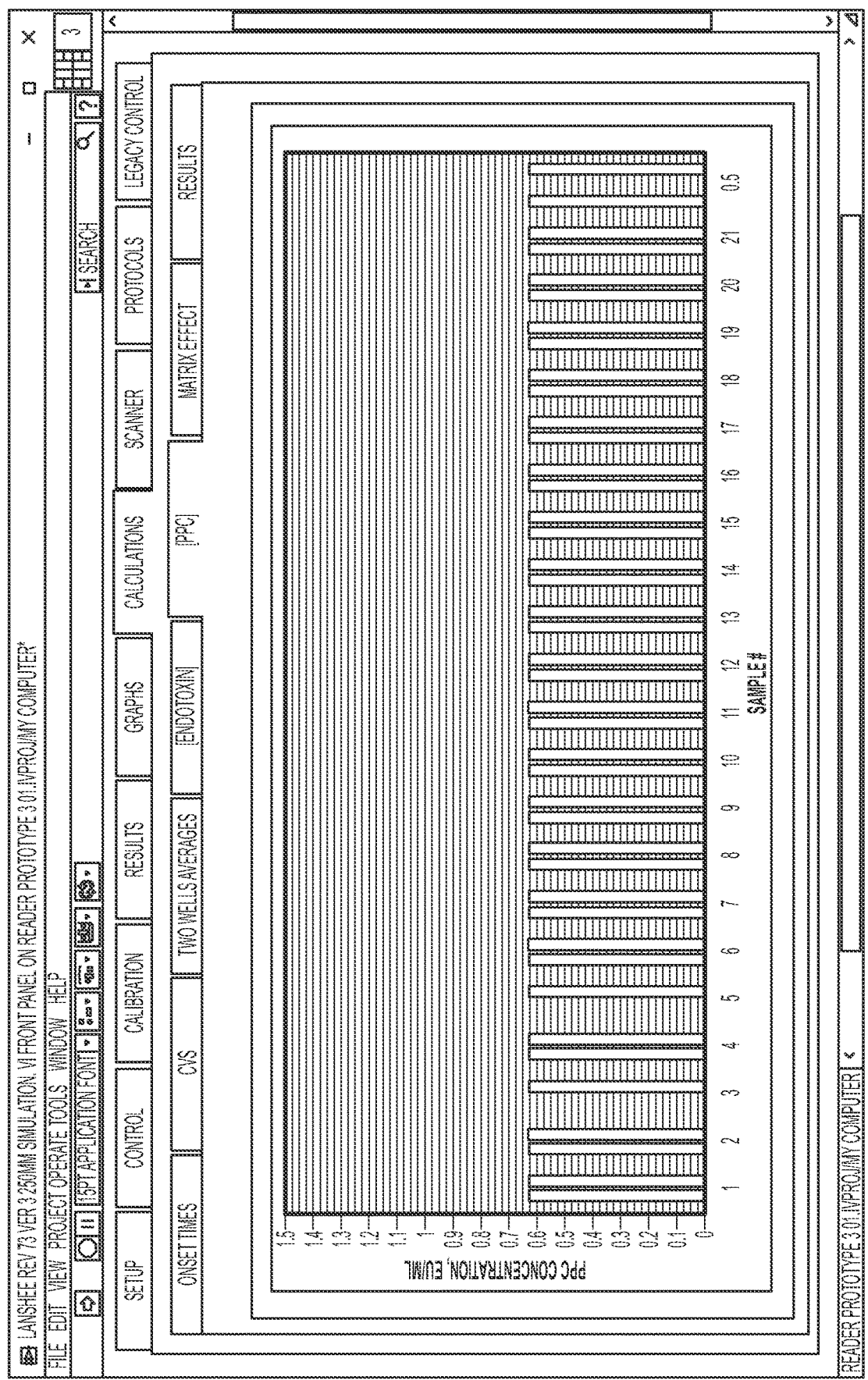
Figure 13:
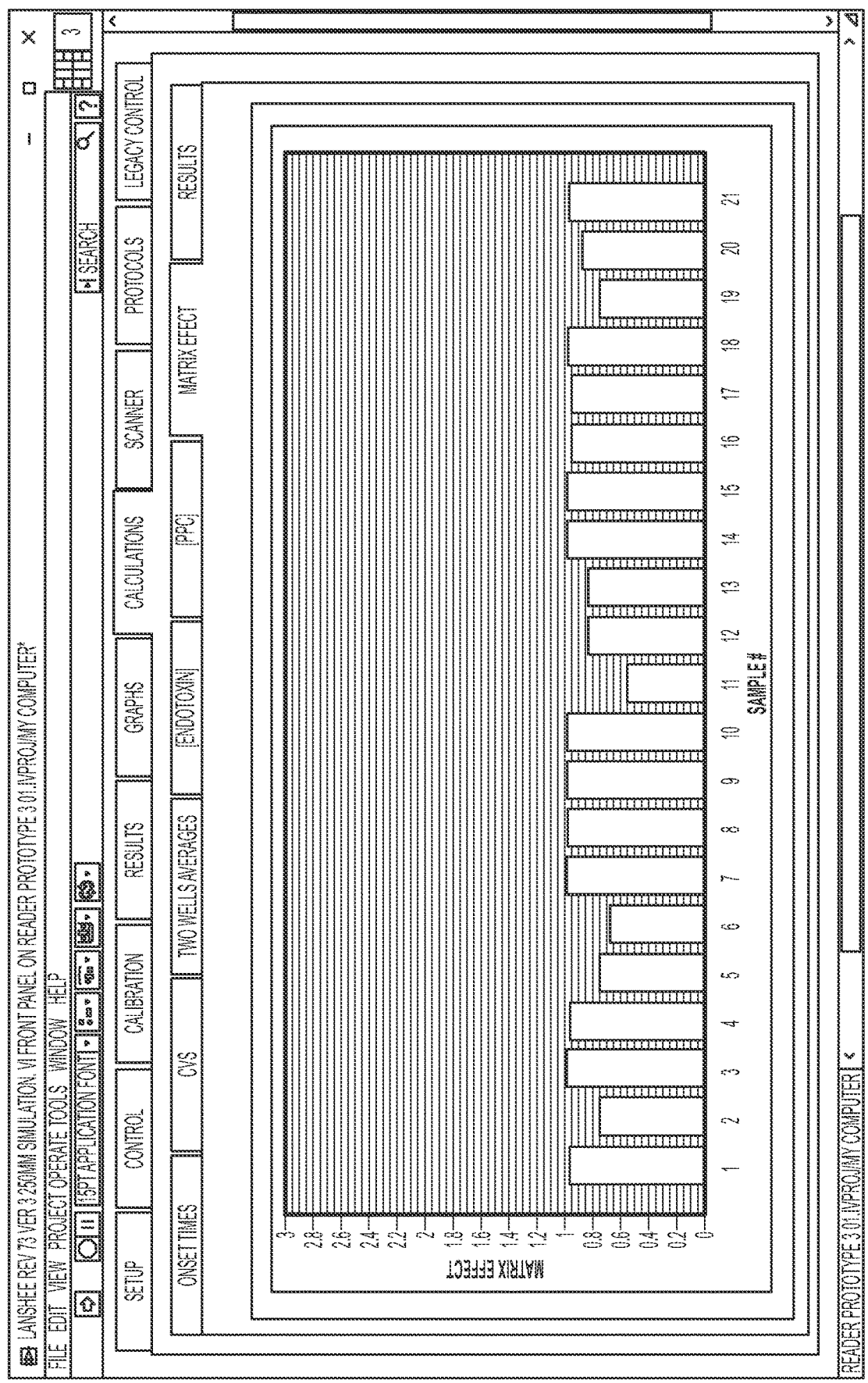

FIG. 7 shows an example view of measured absorbance levels (e.g., in AU) of wells in a microplate being displayed in a side-by-side vertically-oriented manner FIG. 8 shows example views of assessed onset times (e.g., in seconds unit) of wells in a micro-plate being displayed in a side-by-side vertically-oriented manner. FIG. 9 shows example views of two-point coefficient of variation values (e.g., in percentage) of wells in a micro-plate being displayed in a side-by-side vertically-oriented manner FIG. 10 shows example views of measured endotoxin concentration values (e.g., in EU/ml) of wells in a micro-plate being displayed in a side-by-side vertically-oriented manner FIG. 11 shows example views of measured endotoxin concentration values (e.g., in EU/ml) of a given sample (e.g., as an average value of wells for a given group) in a micro-plate being displayed in a side-by-side vertically-oriented manner FIG. 12 shows example views of measured PPC recovery values (e.g., in EU/ml) of wells in a micro-plate being displayed in a side-by-side vertically-oriented manner FIG. 13 shows example views of calculated matrix effect values (e.g., unitless) of wells in a micro-plate being displayed in a side-by-side vertically-oriented manner Computing Environment The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for analysis of a fluid sample for endotoxins. In one exemplary aspect, the units can comprise an analyzer and/or a data analysis computer that comprises one or more computing devices that each comprise a processor 1421 as illustrated in FIG. 14 and described below. As used herein, processor refers to a physical hardware device that executes encoded instructions for performing functions on inputs and creating outputs.

FIG. 14 illustrates an exemplary computer that can be used for executing software for analysis of a fluid sample for endotoxins. As used herein, "computer" may include a plurality of computers. The computers may include one or more hardware components such as, for example, a processor 1421, a random-access memory (RAM) module 1422, a read-only memory (ROM) module 1423, a storage 1424, a database 1425, one or more input/output (I/O) devices 1426, and an interface 1427. Alternatively, and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 1424 may include a software partition associated with one or more other hardware components. It is understood that the components listed above are exemplary only and not intended to be limiting.

Processor 1421 may include one or more processors, each configured to execute instructions and process data to perform one or more functions associated with a computer for executing software to perform an analysis of a fluid sample for endotoxin. Processor 1421 may be communicatively coupled to RAM 1422, ROM 1423, storage 1424, database 1425, I/O devices 1426, and interface 1427. Processor 1421 may be configured to execute sequences of computer program instructions to perform various processes. The computer program instructions may be loaded into RAM 1422 for execution by processor 1421.

RAM 1422 and ROM 1423 may each include one or more devices for storing information associated with operation of processor 1421. For example, ROM 1423 may include a memory device configured to access and store information associated with the computer, including information for identifying, initializing, and monitoring the operation of one or more components and subsystems. RAM 1422 may include a memory device for storing data associated with one or more operations of processor 1421. For example, ROM 1423 may load instructions into RAM 1422 for execution by processor 1421.

Storage 1424 may include any type of mass storage device configured to store information that processor 1421 may need to perform processes consistent with the disclosed embodiments. For example, storage 1424 may include one or more magnetic and/or optical disk devices, such as hard drives, CD-ROMs, DVD-ROMs, or any other type of mass media device.

Database 1425 may include one or more software and/or hardware components that cooperate to store, organize, sort, filter, and/or arrange data used by the computer and/or processor 1421. For example, database 1425 may store data related to the analysis software. The database may also contain data and instructions associated with computer-executable instructions for performing an analysis of a fluid sample for endotoxin and creating a GUI and/or report for the results of the analysis. It is contemplated that database 425 may store additional and/or different information than that listed above.

I/O devices 1426 may include one or more components configured to communicate information with a user associated with computer. For example, I/O devices may include a console with an integrated keyboard and mouse to allow a user to maintain a database of fluid sample and endotoxin information, and the like. I/O devices 1426 may also include a display including a graphical user interface (GUI) for outputting information on a monitor. I/O devices 1426 may also include peripheral devices such as, for example, a printer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1427 may include one or more components configured to transmit and receive data via a communication network, such as the Internet, a local area network, a workstation peer-to-peer network, a direct link network, a wireless network, or any other suitable communication platform. For example, interface 1427 may include one or more modulators, demodulators, multiplexers, demultiplexers, network communication devices, wireless devices, antennas, modems, and any other type of device configured to enable data communication via a communication network.

The figures illustrate the architecture, functionality, and operation of possible implementations of systems, methods and computer program products according to various implementations of the present invention. In this regard, each block of a flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

Any combination of one or more computer readable medium(s) may be used to implement the systems and methods described hereinabove. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to implementations of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain and to illustrate improvements over the present state of the art in claimed invention.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not intended to be exhaustive or to limit the embodiments to the precise forms disclosed. It will be apparent to one of ordinary skill in the art that many modifications and variations are possible in view of the above teachings.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A computer-implemented method to generate visualizations of endotoxin concentrations in a fluid sample, the method comprising:

generating, by a processor, for a graphical user interface or for a report, to be displayed on a stationary or mobile computing device, a graphical visualization, from a data set that identifies an optical density (OD) reading of a microplate comprising a plurality of optical wells, each optical well containing a fluid sample, said graphical visualization comprising a vertically-oriented bar graph having a plurality of vertical bars with at least one vertically-oriented bar graph for each optical well of the microplate, wherein the processor causes the vertically-oriented bar graph corresponding to the optical well of the microplate to increase vertically over time as a reaction between Limulus Amoebocyte Lysate (LAL) and bacterial endotoxin takes place in the optical well of the microplate, wherein a greater amount of endotoxin present in the optical well, the faster the reaction occurs with the LAL reagent, and subsequently the faster the processor causes the associated vertically-oriented bar graph to increase on the graphical visualization.

2. The computer-implemented method of claim 1, further comprising generating, by the processor, a horizontal line on the graphical visualization that represents a threshold OD or an onset OD, wherein a time at which vertically-oriented bar graph corresponding to an optical well reaches or passes the horizontal line is referred to as an "onset time" or a "reaction time" of the fluid sample in the optical well corresponding to the vertically-oriented bar graph that reached or passed the horizontal line.

3. The computer-implemented method of claim 1, wherein once the vertically-oriented bar graph reaches the horizontal line, the processor causes a color of the vertically-oriented bar graph to change from a first color to a second color.

4. The computer-implemented method of claim 1, further comprising generating, by the processor, vertically-oriented bar graphs representing endotoxin standards and negative controls that are also displayed on the graphical visualization.

5. The computer-implemented method of claim 4, wherein the vertically-oriented bar graphs representing endotoxin standards are labeled by the processor in a first color, vertically-oriented bar graphs representing negative controls are labeled by the processor in a second color, and the vertically-oriented bar graphs corresponding to the optical wells of the microplate are labeled by the processor in a third color.

6. The computer-implemented method of claim 4, wherein the vertically-oriented bar graphs representing endotoxin standards are labeled by the processor in dark green, the vertically-oriented bar graphs representing negative controls are labeled by the processor in red, and the vertically-oriented bar graphs corresponding to the optical wells of the microplate are labeled by the processor in blue until they reach a horizontal line generated by the processor on the graphical visualization that represents a threshold OD or an onset OD, at which point the vertically-oriented bar graphs corresponding to the optical wells of the microplate are turned green by the processor.

7. The computer-implemented method of claim 1, further comprising generating, by the processor, vertically-oriented bar graphs representing positive product controls on the graphical visualization.

8. The computer-implemented method of claim 7, wherein the vertically-oriented bar graphs representing positive product controls are labeled by the processor using a same color as used by the processor to label the vertically-oriented bar graphs corresponding to the optical wells of the microplate once the vertically-oriented bar graphs corresponding to the optical wells of the microplate reach a horizontal line generated by the processor on the graphical visualization, wherein the horizontal line represents a threshold OD or an onset OD.

9. The computer-implemented method of claim 1, wherein the positive product controls are calculated by the processor as: endotoxin concentration in PPC subtracted by endotoxin concentration in sample and then divided by actual endotoxin concentration of a 0.5 EU/mL standard.

10. A system for testing of endotoxin in inject-able drug product or water, the system comprising:
   a processor; and
   a memory having instructions stored thereon, wherein execution of the instructions by the processor, cause the processor to:
      continuously obtain one or more data sets associated with measurement of a multi-well micro plate during acquisition of measurement of the multi-well micro plate, wherein each measurement is associated with a measured level of endotoxins reactions of i) endotoxins in an acquired sample of inject-able drug product or water to ii) one or more test reagents over time, and wherein the data set comprises a current measured level of endotoxin reactions for each well of the multi-well micro plate, wherein the multi-well micro plate comprises at least 96 wells; and
      singularly display, in a pane of a graphical user interface, from the obtained data set, a side-by-side graph comprising a plurality of visual elements, wherein each visual element of the plurality of visual elements is associated with the current measured level for the each well of the at least 96 wells of the multi-well micro plate,
   wherein each visual element of the plurality of visual elements comprises a vertically oriented bar that is configured to display data values spanning a range between a minimum value and a maximum value, wherein each of the minimum value and maximum value are aligned with a respective first and second horizontal line,
   wherein the display further comprises a visual element comprising a third horizontal line at a value that indicates an onset threshold of an endotoxin reaction for each, or among group of wells, of the at least 96 wells of the multi-well micro plate, and
   wherein the side-by-side graph of the at least 96 wells of the multi-well micro plate provides simultaneous comparison of a progress of endotoxin reaction in, or among group of wells of, the at least 96 wells of the multi-well micro plate to test endotoxin in the acquired sample of inject-able drug product or water.

11. The system of claim 10, wherein the side-by-side graph of the at least 96 wells of the multi-well micro plate provides indication of an improperly configured well, and wherein the indication is used to retest, or to evaluate retesting of, the sample of inject-able drug product or water in the improperly configured well in a subsequent test.

12. The system of claim 10, wherein the one or more data sets associated with measurement of the multi-well micro plate having the at least 96 wells are continuously obtained and displayed at a pre-defined interval of at least once a second, wherein the interval is fixed to provide for observations of rate of endotoxin reactions in the at least 96 wells or a portion thereof.

13. The system of claim 10, wherein the instructions when executed by the processor cause the processor to:
   receive input from an input device, wherein the input is associated with a cursor of the display;
   determine, in the pane of the graphical user interface, the cursor is placed on a visual element of the plurality of visual elements for at least one from the group consisting of selection of a visual element or for a pre-defined period of time; and
   display, in the pane or in a second pane of the graphical user interface, i) a graph of the measured level of endotoxins reaction(s) over time for one or more wells that the cursor is placed or ii) measure parameter associated with the one or more wells that the cursor is placed.

14. The system of claim 13, wherein the graph of the measured level of endotoxin reaction(s) over time is presented, and wherein the graph comprises one or more kinetic curves over a period of reaction time for the selected well(s).

15. The system of claim 10 further comprising a display, the display having a horizontal pixel elements greater than twice a number of wells of the multi-well micro plate.

16. The system of claim 15, wherein the display has a set of vertical pixel elements, and wherein each of the plurality of visual elements spans at least 80% of the set of vertical pixel elements.

17. The system of claim 10, wherein a portion of the at least 96 wells of the multi-well micro plate includes a set of one or more standard wells, including a first standard well and a second standard well, wherein the visual elements associated with the first well and second well has a color that is different from the remainder of the at least 96 wells of the multi-well micro plate.

18. The system of claim 10, further comprising:
   a sensor system configured to interrogate the at least 96 wells of the multi-well micro plate for measurement of the measured level of endotoxin reactions in the multi-well micro plate, wherein the sensor system comprises one or more sensors selected from the group consisting of an absorbance sensor, a fluorescence sensor, and a luminescence sensor.

19. The system of claim 10, wherein the measured level of endotoxin reactions comprises values associated with a measured change in transparency of the acquired sample of inject-able drug product or water associated with a reaction with the one or more test reagents.

20. The system of claim 19, wherein the measured level comprises values associated with a measured change in optical properties selected from the group consisting of, absorbance, luminance, fluorescent, and a combination thereof, of the acquired sample of inject-able drug product or water associated with a reaction with the one or more test reagents.

21. The system of claim 10, wherein the plurality of visual elements comprise a first set of visual elements associated with standard wells, a second set of visual elements associated with standard wells, a third set of visual elements associated with standard wells, a fourth set of visual elements associated with standard wells, a fifth set of visual elements associated with standard wells, and a sixth set of visual elements associated with standard wells,
- wherein the first set of visual elements has a 50-EU/ml standard,
- wherein the second set of visual elements has a 5-EU/ml standard,
- wherein the third set of visual elements has a 0.5-EU/ml standard,
- wherein the fourth set of visual elements has a 0.05-EU/ml standard,
- wherein the fifth set of visual elements has a 0.005-EU/ml standard, and
- wherein the sixth set of visual elements has a negative control standard.

22. The system of claim 10, wherein the instructions when executed by the processor cause the processor to:
- receive input from an input device, wherein the input is associated with a selection of measurement parameter of the multi-well micro plate selected from the group consisting of measured onset time, measured endotoxin concentration, measured positive product control (PPC) recovery, and determined matrix effect;
- obtain one or more second data sets associated with selected parameter; and
- display, in the pane or in a second pane of the graphical user interface, a second plurality of visual elements associated with the selected parameter, wherein the second plurality of visual elements have a number corresponding to the at least 96 wells, or a portion thereof.

23. A method to monitor testing of endotoxin in inject-able drug product or water, the method comprising:
- obtaining, by a processor, one or more data sets associated with measurement of a multi-well micro plate, where each measurement is associated with a measured level of endotoxins in an acquired sample of inject-able drug product or water over time, wherein the data set comprises a current measured level for each well of the multi-well micro plate, wherein the multi-well micro plate comprises at least 96 wells; and
- singularly displaying, by the processor, in a pane of a graphical user interface, from the obtained data set, a side-by-side graph comprising a plurality of visual elements, wherein each visual element of the plurality of visual elements is associated with a current measured level of each of the at least 96 wells of the multi-well micro plate,
- wherein each visual element of the plurality of visual elements comprises a vertically oriented bar that is configured to span data values ranging between a minimum and a maximum value, wherein each of the minimum value and maximum value are coincident with a first and second horizontal line,
- wherein the display further comprises a visual element comprising a third horizontal line at a measured value that indicates onset threshold for each of the at least 96 wells of the multi-well micro plate, and
- wherein the side-by-side graph of the at least 96 wells of the multi-well micro plate provides simultaneous comparison of speed of reaction in, or among group of wells of, the at least 96 wells of the multi-well micro plate to monitor testing of endotoxin in the acquired sample of inject-able drug product or water.

24. A non-transitory computer readable medium having instructions stored thereon, wherein execution of the instructions by a processor, cause the processor to:
- obtain one or more data sets associated with measurement of a multi-well micro plate, where each measurement is associated with a measured level of endotoxins in an acquired sample of inject-able drug product or water over time, wherein the data set comprises a current measured level for each well of the multi-well micro plate, wherein the multi-well micro plate comprises at least 96 wells; and
- singularly display, in a pane of a graphical user interface, from the obtained data set, a side-by-side graph comprising a plurality of visual elements, wherein each visual element of the plurality of visual elements is associated with a current measured level of each of the at least 96 wells of the multi-well micro plate,
- wherein each visual element of the plurality of visual elements comprises a vertically oriented bar that is configured to span data values ranging between a minimum and a maximum value, wherein each of the minimum value and maximum value are coincident with a first and second horizontal line,
- wherein the display further comprises a visual element comprising a third horizontal line at a measured value that indicates onset threshold for each of the at least 96 wells of the multi-well micro plate, and
- wherein the side-by-side graph of the at least 96 wells of the multi-well micro plate provides simultaneous comparison of speed of reaction in, or among group of wells of, the at least 96 wells of the multi-well micro plate to monitor testing of endotoxin in the acquired sample of inject-able drug product or water.

25. The non-transitory computer readable medium of claim 24, wherein the instructions when executed by the processor further cause the processor to:
- control a sensor system configured to interrogate, and acquire measurement of, the at least 96 wells of the multi-well micro plate for measurement of the measured level of endotoxin reactions in the multi-well micro plate, wherein the sensor system comprises one or more sensors selected from the group consisting of an absorbance sensor, a fluorescence sensor, and a luminescence sensor.

* * * * *